US009017744B2

(12) United States Patent
Kashimura et al.

(10) Patent No.: US 9,017,744 B2
(45) Date of Patent: *Apr. 28, 2015

(54) METHOD OF USING ISOMALTULOSE TO SUPPRESS BLOOD GLUCOSE LEVEL INCREASE

(75) Inventors: Jun Kashimura, Chigasaki (JP); Yukie Nagai, Chigasaki (JP); Tadashi Ebashi, Chigasaki (JP)

(73) Assignee: Mitsui Sugar Co., Ltd., Tokyo (JP)

( * ) Notice: Subject to any disclaimer, the term of this patent is extended or adjusted under 35 U.S.C. 154(b) by 40 days.

This patent is subject to a terminal disclaimer.

(21) Appl. No.: 12/832,933

(22) Filed: Jul. 8, 2010

(65) Prior Publication Data
US 2011/0008486 A1 Jan. 13, 2011

Related U.S. Application Data

(62) Division of application No. 10/715,125, filed on Nov. 18, 2003, now abandoned.

(30) Foreign Application Priority Data

Nov. 18, 2002 (JP) .................. 2002-334032
Mar. 31, 2003 (JP) .................. 2003-096395
Nov. 17, 2003 (JP) .................. 2003-386594

(51) Int. Cl.
A23L 1/29 (2006.01)
A23L 1/236 (2006.01)
A21D 2/18 (2006.01)
A23L 1/307 (2006.01)
A23L 2/60 (2006.01)
A61K 31/70 (2006.01)

(52) U.S. Cl.
CPC ............... *A23L 1/2363* (2013.01); *A21D 2/181* (2013.01); *A23L 1/307* (2013.01); *A23L 2/60* (2013.01); *A23V 2002/00* (2013.01); *A61K 31/70* (2013.01)

(58) Field of Classification Search
None
See application file for complete search history.

(56) References Cited

U.S. PATENT DOCUMENTS

| 4,374,841 | A | 2/1983 | Descamps et al. |
| 4,400,387 | A | 8/1983 | Rosseels et al. |
| 4,556,429 | A | 12/1985 | Takazoe et al. |
| 4,587,119 | A | 5/1986 | Bucke et al. |
| 4,971,798 | A | 11/1990 | Coia et al. |
| 5,360,621 | A | 11/1994 | Mentink et al. |
| 6,761,922 | B2 | 7/2004 | Ishii |
| 2002/0192344 | A1 | 12/2002 | Brendel et al. |
| 2003/0180432 | A1 | 9/2003 | Shimizu et al. |
| 2003/0199728 | A1 | 10/2003 | Kashimura |
| 2004/0219141 | A1 | 11/2004 | Kashimura et al. |
| 2011/0008486 | A1 | 1/2011 | Kashimura et al. |
| 2011/0009358 | A1 | 1/2011 | Kashimura et al. |

FOREIGN PATENT DOCUMENTS

| CN | 1553805 A | 12/2004 |
| DE | 3818884 A1 | 1/1989 |
| EP | 1421859 A1 | 5/2004 |
| EP | 1424074 A1 | 6/2004 |
| GB | 2 206 582 A | 1/1989 |
| JP | 61-070945 | 4/1986 |
| JP | 62-051616 | 3/1987 |
| JP | 62-74276 | 4/1987 |
| JP | 63-112963 | 5/1988 |
| JP | 64-085058 | 3/1989 |
| JP | 02-079955 | 3/1990 |
| JP | 03-172136 | 7/1991 |
| JP | 05-252897 | 10/1993 |
| JP | 06-100453 | 4/1994 |
| JP | 06-128161 | 5/1994 |
| JP | 06-245735 | 9/1994 |
| JP | 08-133970 | 5/1996 |
| JP | 08-283169 | 10/1996 |
| JP | 08-289783 | 11/1996 |
| JP | 11-89524 | 4/1999 |
| JP | 2000-300212 | 10/2000 |
| JP | 2000-0067771 | 11/2000 |
| JP | 4048166 | 2/2008 |
| KR | 2000-006771 | 11/2000 |
| KR | 2002-0034209 | 5/2002 |
| WO | 98/04156 | 2/1998 |

(Continued)

OTHER PUBLICATIONS

Rhinehart, B. L., et al. JPET (1987), 241(3); pp. 915-920.*

(Continued)

Primary Examiner — Kevin S Orwig
(74) Attorney, Agent, or Firm — Griffin & Szipl, P.C.

(57) ABSTRACT

A method for reducing blood glucose level increase is provided that includes: providing a reducer of blood glucose level increase, wherein the reducer comprises isomaltulose; having an individual ingest the reducer; and having the individual consume a carbohydrate having an α-1,6-glucosyl bond ratio of from 0% to less than 50% relative to the total bonds among constituent saccharides, wherein the reducer is ingested before or after or simultaneously with consuming the carbohydrate, and wherein the reducer reduces an increase in the individual's blood glucose level caused by consuming the carbohydrate. The reducer of blood glucose level increase includes isomaltulose (PALATINOSE™) as an active ingredient so that when the reducer is ingested and a carbohydrate having an α-1,6-glucosyl bond ratio of from 0% to less than 50% relative to the total bonds among constituent saccharides is consumed, an increase in blood glucose level caused by ingesting the carbohydrate is reduced.

16 Claims, 8 Drawing Sheets

(56) References Cited

FOREIGN PATENT DOCUMENTS

| WO | 01/25263 | 4/2001 |
|---|---|---|
| WO | 03/022288 A1 | 3/2003 |

OTHER PUBLICATIONS

Toshinao, G., et al. J. Jap. Soc. Nutr. Food Sci. (1983), 36(3); pp. 169-173.*
Kawai, K. et al. Endocrinol Japon. (1985), 32(6); pp. 933-936.*
Jenkins, D. J. A., et al. Br. Med. J. (1978), 1; pp. 1392-1394.*
Günther, S., et al. Arch. Biochem. Biophys. (1998), 354(1); pp. 111-116.*
Harper's Biochemistry, Twenty-fifth edition, 2001, pp. 227-233, w/ English translation pp. 210-217).
Textbook of Pharmacology, 1982, pp. 412-415, with English translation.
Suzuki, Masashige et al., "Effects of Dietary Palitinose and Reduced-Palitinose on Body Energy Composition," J. Clin. Biochem. Nutr. 13, 117-125, 1992.
Hamanaka, Kenji, "Physiological Function of Paltinose and Its Utilization to Sport, Diet Foods," Food and Development, vol. 33, No. 11, Health Industry News, 1998, pp. 18-19.
Tsuyuki, Kenichiro, "Characteristics of Paltinose," Journal of Japanese Council for Advanced Food Ingredients Research, Advanced Food Research, 1999, pp. 53-59.
Lugwig, David S. et al., "High Glycemic Index Foods, Overeating and Obesity," Pediatrics vol. 103 No. 3, Mar. 1999.
European Search report issued in a counterpart European application No. 10 00 7324, completed Aug. 31, 2010 and mailed Sep. 14, 2010.
Sean Mark, "What Creates Fat Accumulation?," Aug. 2, 2011, at http://www.livestrong.com/article/508559-what-creates-fat-accumulation/, downloaded Oct. 4, 2011, 3 pages, filed in co-pending related application as Exhibit A.
"Facts about Fat," at http://www.brianmac.co.uk/fat.htm, last modified Sep. 30, 2011, downloaded Oct. 4, 2011, 5 pages, filed in co-pending related application as Exhibit B.
H. Shinohara et al., Effects of Indigestible Dextrin-containing Green Tea on Blood Glucose Level in Healty Human Subjects, Kenko/Eiyosyokuhim Kenkyu, vol. 2, No. 1, 52-56 (1999).
O. Kajimoto et al., Beneficial effects of new indigestible dextrin-containing beverage on lipid metabolism and obesity-related parameters, Kenko/Eiyosyokuhim Kenkyu, vol. 3, No. 3, 47-58 (2000).
K. Sanai et al., Inhibition of Sucrose Digestion and Absorption by L-Arabinose in Rats, Nihon Eiyo/Syokuryo Gakkai Shi (The Journal of JSNFS), vol. 50, No. 2, 133-137 (1997).
Y. Deguchi et al., Effects of Extract of Guava Leaves on the Development of Diabetes in the db/db Mouse and on the Postprandial Blood Glucose of Human Subjects, Nihon Nougei Kagaku Kaishi, vol. 72, No. 8, 923-931 (1998).
K. Kawai et al., Usefulness of Palatinose as a Caloric Sweetener for Diabetic Patients, Hormone and Metabolic Research, 21, 338-340 (1989).
T.M.S. Wolever et al., The use of the blycemic index in predicting the blood glucose response to mixed meals, The American Journal of Clinical Nutrition, 43 (January), 167-172 (1986).
T. Goda et al., Hydrolysis of Palatinose by Rat Intestinal Sucrase-Isomaltase Complex, Nihon Eiyo/Syokuryo Gakkai Shi, vol. 36, No. 3, 169-173 (1983).
ILSI Europe Concise Monograph Series, [Sugar and Nutrition/health, Evaluation fo a new finding], 8-12 (1998).
M. Suzuki, Carbohydrate nutrition and health, Kagaku to Kogyo, vol. 61, No. 1, 17-24 (1987).
New Food Industry, vol. 31, No. 10, 9-15 (1989).
International Search Report in Japanese for PCT/JP03/14675, completed Feb. 18, 2004, and mailed Mar. 2, 2004.
Patent Abstracts of Japan, JP 01269483 A, published Oct. 26, 1989, Mitsui Sugar Co., Ltd.
International Preliminary Report on Patentability, mailed Jul. 7, 2005 in corresponding PCT/JP2003/014675.
International Search Report in corresponding PCT/JP2003/014675 completed Feb. 18, 2004 and mailed Mar. 2, 2004.
Patent Abstracts of Japan, vol. 011, No. 273, of publication No. 62074276, Apr. 6, 1987.
Kawai et al., "Changes in Blood Glucose and Insulin After an Oral Palatinose Administration in Normal Subjects", 1985, abstract only.
European Search Report in corresponding application No. 03 77 2878 completed Nov. 4, 2005 and mailed Nov. 11, 2005.
Notice of Rejection of corresponding Chinese patent application No. 200380103475.3 dated Mar. 3, 2006.
International Search Report issued in corresponding application No. PCT/JP03/14675, completed Feb. 18, 2004 and mailed Mar. 2, 2004.
Office Action issued in corresponding Australian Patent Application No. 2003280856, dated Aug. 23, 2007.
Isomalt—Online Edition: "Combined Compendium of Food Additive Specifications" of the website www.fao.org on Sep. 22, 2008, previously filed as Exhibit B on Oct. 16, 2008.
"About Glycemic Index," http://www.glycemicindex.com/aboutGIprint.htm, downloaded Sep. 23, 2008, previously filed as Exhibit E on Oct. 16, 2008.
New Food Industry, vol. 31, No. 10, 9-15 (1989) with partial English translation.
Webster's Ninth New Collegiate Dictionary, p. 210 (1990).
M. Chen et al., Comparative Pharmacokinetics and Pharmacodynamic Target Attainment of Ertapenem in Normal-Weight, Obese, and Extremely Obese Adults, 50 Antimicrobial Agents and Chemotherapy 1222-1227 (2006), (filed herewith as "Exhibit G").
Kenneth A. Skau, Teaching Pharmacodynamics: An Introductory Module on Learning Dose-Response Relationships, 68 American Journal of Pharmaceutical Education 1-6 (2004), (filed herewith as "Exhibit H").
New Food Industry article "Reference 19", vol. 31, pp. 9-15 (1989).
Lina, B.A.R., et al. (May 2002) Food and Chemical Toxicology. 40; 1375-1381.
Exhibit A1, Honey Tea Menu published in 2010, available at http://www.athenaeumhotel.com/food/offers/honey_tea_menu/menu.aspx (downloaded Jan. 19, 2012, four pages).
Exhibit B1, M.B. Battaglini et al., Determination of Glucides by G.L.C. and its Possibilities for Honey Qualification, APIACTA (1972), four pages.
Exhibit C1, Jonathan W. White Jr. et al., Composition of Honey. IV. Identification of the Disachharides, 80 Arch. Biochem. Biophys. 386-392 (1959).
Exhibit D1, Cargill™ Application for the Approval of Isomaltulose (2003), at ; http://www.food.gov.uk/multimedia/pdfs/isomaltulose.pdf (downloaded Jan. 22, 2012).
Arthur Allen, Does Animal Testing Work?, at http://www.slate.com/articles/health_and_science/medical_examiner/2006/06/of_mice_or_men.html (2006) three pages.
Palatinose™—The only toothfriendly sugar for optimized energy supply, at http://www.beneo-palatinit.com/en/Food_Ingredients/Isomaltulose/What_is_Isomaltulose/FAQ/ (last modified Sep. 18, 2009),twelve pages.
GRAS Notification—Exemption Claim for Isomaltulose (Palatinose™), (2005), with cover letter, at http://www.accessdata.fda.gov/scripts/fcn/gras_notices/grn000184.pdf.
Jun Kashimura and Yuki Nagai, "Addition Ratio of Palatinose and Body Fat Accumulation in Mice," 13 Food Sci. Technol. Res. 81-84 (2007).
"Palatinose", at http://www.chemblink.com/products/58166-27-1.htm (2008).
Davis's Drug Guide : Pediatric Dosage Calculations, at http://www.drugguide.com/ddo/ub/view/Davis-Drug-Guide/ (2010).
E. Shafrir et al., A Useful List of Spontaneously Arising Animal Models of Obesity and Diabetes, 296 American Journal of Physiology, Endocrinology and Metabolism E1450-E1452 (2009).
B. Martin et al., "Control" Laboratory Rodents are Metabolically Morbid: Why it Matters, 107 PNAS 6127-6133 (2010).

(56) References Cited

OTHER PUBLICATIONS

I. MacDonald et al., The Bio-availability of Isomaltulose in Man and Rat, 28 Nutrition Reports International (1983), abstract.
http://www.beneo-palatinit.com/en/Food_Ingredients/Isomaltulose/What_is_Isomaltulose/FAQ/#WhatmakesPalatinosespecial (2010), which corresponds to "Exhibit A2.".
"A Functional, Low Glycaemic Index Carbohydrate to Aid Fat Loss or Support Carbohydrate Loading for Performance" (2012), at http://www.rosnutrition.com/ie/knowledgecentre/writeup/isomaltulose (downloaded Aug. 9, 2013).
Stacey Hugues, "Honey or Sugar: Which is Better for Diabetics?," at http://diabetes.about.com/od/dieticiansadvice/a/Honey-Or-Sugar-Which-Is-Better-For-Diabetics.htm?p=1 (last updated Oct. 27, 2010).
Charles E. Ophardt, "Enzyme Inhibitors" (2003), at http://www.elmhurstedu/~chm/vchembook/573inhibit.html (downloaded Aug. 16, 2013).
Office Action issued in co-pending related U.S. Appl. No. 12/832,944 dated May 8, 2013.
Kawai, K. et al. "Changes in Blood Glucose and Insulin after an Oral Palatinose Administration in Normal Subjects," Endocrinol Japon (1985), 32 (6); abstract previously provided on IDS, Aug. 27, 1985, pp. 933-936.
Examiner-Initiated Interview Summary mailed Dec. 4, 2013 discussing the telephone conference of Nov. 26, 2013.
A. Raben, Should Obese Patients be Counseled to Follow a Low-glycaemic Index Diet? No. 3 Obesity Reviews 245-256 (2002).
Dietary Guidelines for Americans 2010, U.S. Department of Health and Human Services (2010).
Dietary Guidelines for Americans 2005, U.S. Department of Health and Human Services (2005).
"Glycemic Response," at http://www.caloriecontrol.org/health-professional-library/glycemic-index (2013).
"Nutrition Facts and Analysis for Isomaltulose," at http://nutritiondata.self.com/facts/custom/2818254/2?print=true (2012).
Office Action mailed Aug. 4, 2014 in related U.S. Appl. No. 12/832,944.
Jenkins, D. et al., "Dietary fibres, fibres analogues, and glucose tolerance: importance of visocosity" British Medical Journal, (1978), 1, pp. 1392-1394.

* cited by examiner

METHOD OF USING ISOMALTULOSE TO SUPPRESS BLOOD GLUCOSE LEVEL INCREASE

This application is a Divisional Application of U.S. patent application Ser. No. 10/715,125 (now abandoned), filed on Nov. 18, 2003, which claims priority from Japanese Patent Application Nos. 2002-334032, 2003-096395, and 2003-386594, filed on Nov. 18, 2002, Mar. 31, 2003 and Nov. 17, 2003, respectively. The entire disclosures of the above patent applications are hereby incorporated by reference.

FIELD OF THE INVENTION

The present invention relates to a reducer of blood glucose level increase, a reducer of body fat accumulation, a food material, a method for reducing blood glucose level and a method for reducing body fat accumulation.

RELATED BACKGROUND OF THE INVENTION

As a constituent for reducing blood glucose level increase, there have been known an extract from Gymnema Sylvestre leaves (JP Tokkai S64-85058, JP Tokkai H2-79955), an extract from Gymnema Inodrum (JP Tokkai H5-252897), and an extract from Gymnema Chingen (JP Tokkai H6-245735). They are considered to reduce blood glucose level increase because of an effect of reducing glucose absorption. Triterpene glycoside (JP Tokkai H6-128161) contained in Gymnema Inodrum is also reported to have the effect of reducing glucose absorption.

Monoterpene glycoside is known to have an effect of reducing blood glucose level increase through a sucrase inhibition effect (JP Tokkai H6-100453). Examples of such monoterpene glycoside include a betaine from a sugar beet (JP Tokkai H8-133970), a saponin mixture from Alaria elata (JP Tokkai H8-283169), and an α-glucosidase inhibitor (JP Tokkai H8-289783).

Additionally, there has been recently reported carbohydrate having an effect of reducing blood glucose level increase. Indigestible dextrin is known to show an effect of reducing blood glucose level increase after food intake for a person with easily rising blood glucose level (Kenko/Eiyosyokuhin Kenkyu, Vol. 2, No. 1, 52-56 (1999)), and to have an influence on fat metabolism (Kenko/Eiyosyokuhin Kenkyu, Vol. 3, No. 3, 47-58 (2000)). L-arabinose is also demonstrated to inhibit specifically the activity of small intestine sucrase which decomposes sucrose (Nihon Eiyo/Syokuryo Gakkai Shi (The Journal of JSNFS), Vol. 50, No. 2, 133-137 (1997)).

Although not carbohydrate, a hot water extract from Guava leaves, a plant extract, is known to inhibit the activities of carbohydrate degrading enzymes, such as maltase, sucrase and α-amylase. It is also known that its inhibition effect is particularly stronger for α-amylase than for the other two enzymes. Hence, it is demonstrated to reduce blood glucose level increase after food intake (Nippon NogeiKagaku Kaishi, Vol. 72, No. 8, 923-931 (1998)).

SUMMARY OF THE INVENTION

However, the Gymnema extract etc. taste so bitter as to block sweet taste, and hence can not be used without a particular treatment. The indigestible dextrin and L-arabinose, though carbohydrate, are difficult to be digestibly absorbed, and sometimes cause diarrhea when they are ingested in a large amount. A substance having an effect of inhibiting sucrase activity is pointed out that, when ingested together with sucrose, it allows the sucrose to reach a large intestine without decomposition. In other words, all the above substances demonstrating the effect of reducing blood glucose level increase have various problems such as inconvenience at use and limited application.

Therefore, a reducer of blood glucose level increase which is free from unpleasant taste such as bitter taste and which can be ingested as a safe food has been desired. Further, a plant extract is not usually ingested as food, and L-arabinose is a food additive. Therefore, a method for reducing blood glucose level increase employing a safe food material usually ingestible as food has been desired.

An object of the present invention is to provide a reducer of blood glucose level increase which can solve the above problems in the prior art.

The present inventors have made a diligent study and found out that a combination of certain substance causing the blood glucose level increase and PALATINOSE™ (6-O-alpha-D-Glucopyranosyl-D-fructofuranose, also known generically as "isomaltulose") can be ingested, while solving the problems, to reduce blood glucose level increase caused by the substance, and have completed the invention.

Namely, the invention provides a reducer of blood glucose level increase comprising PALATINOSE™ (isomaltulose) as an active ingredient, wherein the reducer is ingested before or after or simultaneously with consuming a carbohydrate having an α-1,6-glucosyl bond ratio of from 0% to less than 50% relative to the total bonds among constituent saccharides, and wherein the reducer reduces an increase in blood glucose level caused by consuming said carbohydrate(or a reducer of blood glucose level increase for reducing a blood glucose level increase caused by consuming a carbohydrate having an α-1,6-glucosyl bond ratio of from 0% to less than 50% relative to the total bonds among constituent saccharides characterized by comprising PALATINOSE™ (isomaltulose) as an active ingredient and being ingested before or after or simultaneously with consuming the carbohydrate).

As is reported in Hormone and Metabolic Research, 21, 338-340 (1989) etc., PALATINOSE™ (isomaltulose) is a foodstuff having a low Glycemic Index and causes no sudden increase or decrease in blood glucose level after ingestion [Glycemic Index (GI) is an index which indicates relationship between food and blood glucose level, which is in the news recently, and uses white bread or glucose as a standard food (The American Journal of Clinical Nutrition, 43 (January), 167-172 (1986))]. It has been considered that PALATINOSE™ (isomaltulose) is ingested simultaneously with another carbohydrate to express a change in blood glucose level which is a sum of the change caused by the PALATINOSE™ (isomaltulose) and the carbohydrate. Therefore, PALATINOSE™ (isomaltulose) has been only intended to be used alone as a carbohydrate in a food for reducing blood glucose level increase.

With respect to the coexistence effect of PALATINOSE™ (isomaltulose) and another carbohydrate, there is a report on the relation between PALATINOSE™ (isomaltulose) and sucrose (Nihon Eiyo/Syokuryo Gakkai Shi(Journal of Japanese Society of Nutrition and Food Science), Vol. 36, No. 3, 169-173 (1983)). According to the report, since sucrase (sucrose α-D-glucohydrolase) catalyzes to decompose sucrose into glucose and fructose and is specific for sucrose or maltose as the substrate, it does not catalyze to decompose PALATINOSE™ (isomaltulose) or isomaltose having different bond of the same combinations of the constituent sugars to sucrose or maltose, respectively. Therefore, it is reported that, when sucrose and PALATINOSE™ (isomaltulose) coexist, they are catalyzed independently to decompose without mutual influence.

On the contrary, isomaltase (oligo-1,6-glucosidase), which is an enzyme catalyzing decomposition of PALATINOSE™ (isomaltulose) inside a digestive tract, catalyzes to decompose a carbohydrate having an α-1,6-glucosyl bond such as isomaltose, panose and isomaltotriose. Hence, it is reported that, when PALATINOSE™ (isomaltulose) and these carbohydrates coexist, they competitively inhibit decomposition reaction catalyzed by the enzyme one another, resulting in their respective slow decomposition rates (Nihon Eiyo/Syokuryo Gakkai Shi(Journal of Japanese Society of Nutrition and Food Science), Vol. 36, No. 3, 169-173 (1983)). It has been concluded from the report that, through competitive inhibition by isomaltase, PALATINOSE™ (isomaltulose) can reduce the blood glucose level increase caused by consuming a carbohydrate having an α-1,6-glucosyl bond ratio of 50% or more relative to the total bonds among constituent saccharides. However, PALATINOSE™ (isomaltulose) is not supposed to be able to reduce the blood glucose level increase caused by consuming a carbohydrate having no α-1,6-glucosyl bond including monosaccharide or a carbohydrate having an α-1,6-glucosyl bond ratio of less than 50% relative to the total bonds among constituent saccharides.

Contrary to the recognition, however, the inventors have found out a novel phenomenon that, when palatisose is ingested before or after or simultaneously with consuming a carbohydrate having an α-1,6-glucosyl bond ratio of from 0% to less than 50% relative to the total bonds among constituent saccharides, it can reduce the blood glucose level increase caused by ingesting the carbohydrate.

The present invention provides a reducer of blood glucose level increase comprising PALATINOSE™ (isomaltulose) as an active ingredient, wherein the reducer is ingested before or after or simultaneously with consuming at least one foodstuff being selected from the group consisting of sucrose, wheat flour, starch, dextrin and high fructose corn syrup, and wherein the reducer reduces an increase in blood glucose level caused by consuming the foodstuff (or a reducer of blood glucose level increase for reducing a blood glucose level increase caused by consuming at least one foodstuff selected from the group consisting of sucrose, wheat flour, starch, dextrin and high fructose corn syrup, characterized by comprising PALATINOSE™ (isomaltulose) as the active ingredient and being ingested before or after or simultaneously with consuming the foodstuff).

Starch and dextrin are catalyzed by α-amylase, β-amylase and α-glucosidase (maltase) to decompose to glucose, which is absorbed at small intestine. PALATINOSE™ (isomaltulose), though having a glucosyl group, is demonstrated to be hardly catalyzed by α-glucosidase.

High fructose corn syrup composed of glucose and fructose, a commercial product of saccharide (carbohydrate) composed of monosaccharides, is ingested to give a sudden increase and decrease curve in blood glucose level as is seen in sucrose. It has been considered that high fructose corn syrup, which is composed of the monosaccharides, is not competitive as to catalysis by the decomposition enzyme for PALATINOSE™ (isomaltulose) and is easily absorbed.

It has been generally known that glucose and sucrose cause a sudden increase/decrease curve in blood glucose level. White bread, as well as glucose, is used as a standard to measure a Glycemic Index because starch in the food is digested at a considerably large rate to show a sudden increase/decrease curve in blood glucose level close to that of sucrose or glucose (ILSI Europe Concise Monograph Series, [Nutrition and Health Aspects of Sugars, Evaluation of new findings], pp 8-12 (1998)). Dextrin, a partial decomposition product of starch, is easily supposed to draw a blood glucose level curve similar to that of starch. Therefore, sucrose, glucose, starch and dextrin are representative of carbohydrates which are apt to raise suddenly blood glucose level after ingestion and are used in a wide range of processed foods. High fructose corn syrup, a liquid sugar composed of glucose and fructose which are the constituent saccharides of sucrose, is ingested to show a blood glucose level increase curve similar to that of sucrose.

It has been generally considered that, when PALATINOSE™ (isomaltulose) giving a mild increase/decrease in blood glucose level and a carbohydrate (saccharide) giving a sudden increase/decrease in blood glucose level such as sucrose, glucose, dextrin or starch are simultaneously ingested, sucrose, glucose, dextrin or starch, which is an easily digested carbohydrate, causes sudden increase in glucose level as is the case where it is ingested alone, and that slow changes of glucose level caused by PALATINOSE™ (isomaltulose) simultaneously ingested is not reflected. The consideration is based on the understanding that PALATINOSE™ (isomaltulose) don't cause competitive inhibition because the decomposing enzymes for the above described carbohydrates, which are easily digestible, are significantly different from PALATINOSE™ (isomaltulose) decomposing enzyme (PALATINOSE™ (isomaltulose) is catalyzed to decompose at a rate about one fifth of that of sucrose), and that PALATINOSE™ (isomaltulose) has no influence on the absorption of a monosaccharide such as glucose.

Thus, the invention, that PALATINOSE™ (isomaltulose) is ingested before or after or simultaneously with consuming at least one foodstuff being selected from the group consisting of sucrose, wheat flour, starch, dextrin and high fructose corn syrup to reduce an increase in blood glucose level caused by consuming the foodstuff, provides a completely novel knowledge.

The invention also provides a reducer of blood glucose level increase comprising PALATINOSE™ (isomaltulose) as an active ingredient, wherein the reducer is ingested before or after or simultaneously with consuming food, and wherein the reducer reduces an increase in blood glucose level caused by consuming the food (or a reducer of blood glucose level increase for reducing an increase in blood glucose level caused by consuming food characterized by comprising PALATINOSE™ (isomaltulose) as the active ingredient and being ingested before or after or simultaneously with consuming the food).

The amount of carbohydrate upon ingesting an ordinary food is considered to be 50-150 g per food. And the carbohydrate contained in one feed causes mainly blood glucose level increase after eating. An ordinary food uses food material which contain a lot of carbohydrate such as potatoes, rice products (rice diet, noodles such as Vietnamese pho noodle or rice vermicelli, and rice cake) and wheat products (wheat flour, wheat noodle, bread, baked cake, pizza crust and Japanese pancake). The carbohydrate contained in them is mainly starch. It has been considered that, for ingested PALATINOSE™ (isomaltulose), it is more difficult to reduce an increase in blood glucose level through consuming a carbohydrate in food, which exists with other ingredients in being kneaded with or surrounded by the other ingredients, than to reduce an increase in blood glucose level through consuming a carbohydrate such as monosaccharide and disaccharide, which are consumed as an aqueous solution. Therefore, the fact that PALATINOSE™ (isomaltulose) is ingested to reduce blood glucose level increase after eating provides a completely novel knowledge.

Further, the invention provides a reducer of body fat accumulation comprising PALATINOSE™ (isomaltulose) as an active ingredient, wherein the reducer is ingested before or after or simultaneously with consuming a carbohydrate having an α-1,6-glucosyl bond ratio of from 0% to less than 50% relative to the total bonds among constituent saccharides, and wherein the reducer reduces body fat accumulation resulted from the increase in blood glucose level and insulin secretion caused by ingesting the carbohydrate (or a reducer of body fat accumulation for reducing body fat accumulation resulted from the increase in blood glucose level and insulin secretion amount caused by ingesting a carbohydrate having an α-1,6-glucosyl bond ratio of from 0% to less than 50% relative to the total bonds among constituent saccharides, characterized by comprising PALATINOSE™ (isomaltulose) as the active ingredient and being ingested before or after or simultaneously with consuming the carbohydrate).

Furthermore, the invention provides a reducer of body fat accumulation comprising PALATINOSE™ (isomaltulose) as an active ingredient, wherein the reducer is ingested before or after or simultaneously with consuming at least one foodstuff being selected from the group consisting of sucrose, wheat flour, starch, dextrin and high fructose corn syrup, and wherein the reducer reduces body fat accumulation resulted from the increase in blood glucose level and insulin secretion caused by consuming the foodstuff (or a reducer of body fat accumulation for reducing body fat accumulation resulted from the increase in blood glucose level and insulin secretion amount caused by ingesting at least one foodstuff being selected from the group consisting of sucrose, wheat flour, starch, dextrin and high fructose corn syrup, characterized by comprising PALATINOSE™ (isomaltulose) as the active ingredient and being ingested before or after or simultaneously with consuming the foodstuff).

In addition, the invention provides a reducer of body fat accumulation comprising PALATINOSE™ (isomaltulose) as an active ingredient, wherein said reducer is ingested before or after or simultaneously with consuming food, and wherein the reducer reduces body fat accumulation resulted from the increase in blood glucose level and insulin secretion caused by consuming the food (or a reducer of body fat accumulation for reducing body fat accumulation resulted from the increase in blood glucose level and insulin secretion amount caused by consuming food, characterized by comprising PALATINOSE™ (isomaltulose) as the active ingredient and being ingested before or after or simultaneously with consuming the food).

It is reported that, comparing a case where a combination of a high fat diet with sugar and only a basic diet are alternately ingested with another case where only a high fat diet and a combination of a basic diet with sugar are alternately ingested under the condition of the same nutrition intake in 2 meals per day, body fat amount significantly increases when a high fat diet and sugar are ingested simultaneously (Kagaku to Kogyo, Vol. 61, No. 1, 17-24 (1987)). This is resulted from consequent reactions that the ingested sugar causes blood glucose level increase, secretion of insulin is induced, the insulin activates lipoprotein lipase (LPL) in a fat tissue to allow a neutral fat in blood from the diet to be taken rapidly into a fat cell, which is accumulated as body fat (New Food Industry, Vol. 31, No. 10, 9-15 (1989)). Accordingly, in reverse, inhibition of blood glucose level increase to reduce inducing secretion of insulin can inhibit activation of LPL, resulting in reducing body fat accumulation.

Hence, PALATINOSE™ (isomaltulose) is ingested before or after or simultaneously with consuming carbohydrate to result in a mild increase/decrease curve of blood glucose level, to inhibit activation of LPL and to make accumulating body fat difficult.

Further, the invention provides a method for reducing blood glucose level increase by allowing an individual to ingest the above reducer of blood glucose level increase, and a method for reducing body fat accumulation by allowing an individual to ingest the above reducer of body fat accumulation.

Furthermore, the invention provides food materials as shown in following (1)-(6).

(1) A food material comprising PALATINOSE™ (isomaltulose) and a foodstuff composed of a carbohydrate having an α-1,6-glucosyl bond ratio of from 0% to less than 50% relative to the total bonds among constituent saccharides, wherein the food material reduces blood glucose level increase caused by consuming the foodstuff (or a food material comprising PALATINOSE™ (isomaltulose) and a foodstuff composed of a carbohydrate having an α-1,6-glucosyl bond ratio of from 0% to less than 50% relative to the total bonds among constituent saccharides, characterized in that the food material comprises the PALATINOSE™ (isomaltulose) in an amount necessary to reduce an increase in blood glucose level caused by consuming the foodstuff).

(2) A food material comprising PALATINOSE™ (isomaltulose) and at least one foodstuff being selected from the group consisting of sucrose, wheat flour, starch, dextrin and high fructose corn syrup, wherein the food material reduces blood glucose level increase caused by consuming said foodstuff (or a food material comprising PALATINOSE™ (isomaltulose) and at least one foodstuff being selected from the group consisting of sucrose, wheat flour, starch, dextrin and high fructose corn syrup, characterized in that the food material comprises the PALATINOSE™ (isomaltulose) in an amount necessary to reduce an increase in blood glucose level caused by ingesting the foodstuff).

(3) The food material according to the above (2), wherein the food material is used as a sweetener and the foodstuff is at least one foodstuff being selected from the group consisting of sucrose and high fructose corn syrup.

(4) The food material according to the above (2), wherein the food material is used as a premix material and the foodstuff is at least one foodstuff being selected from the group consisting of sucrose, wheat flour, starch and dextrin.

(5) The food material according to the above (2), wherein the food material is used as a powdery drink and the foodstuff is sucrose.

(6) The food material according to the above (2), wherein the weight (A) of the PALATINOSE™ (isomaltulose) has a ratio of 10% or more relative to the total weight (B) of carbohydrate contained in the food material, and the PALATINOSE™ (isomaltulose) is combined so that the PALATINOSE™ (isomaltulose) is ingested by 5 g or more per 60 kg of body weight of an individual.

Each of the above food material (1)-(6) or a food processed from the food material can be ingested to reduce an increase in blood glucose level caused by consuming the above foodstuff.

Furthermore, the invention provides food material as shown in following (7)-(12).

(7) A food material comprising PALATINOSE™ (isomaltulose) and a foodstuff composed of a carbohydrate having an α-1,6-glucosyl bond ratio of from 0% to less than 50% relative to the total bonds among constituent saccharides, wherein the food material reduces body fat accumulation resulted from the increase in blood glucose level and insulin secretion caused by ingesting the foodstuff.

(8) A food material comprising PALATINOSE™ (isomaltulose) and at least one foodstuff being selected from the group consisting of sucrose, wheat flour, starch, dextrin and high fructose corn syrup, wherein the food material reduces body fat accumulation resulted from the increase in blood glucose level and insulin secretion caused by ingesting the foodstuff.

(9) The food material according to the above (8), wherein the food material is used as a sweetener and the foodstuff is at least one foodstuff being selected from the group consisting of sucrose and high fructose corn syrup.

(10) The food material according to the above (8), wherein the food material is used as a premix material and the foodstuff is at least one foodstuff being selected from the group consisting of sucrose, wheat flour, starch and dextrin.

(11) The food material according to the above (8), wherein the food material is used as a powdery drink and the foodstuff is sucrose.

(12) The food material according to the above (8), wherein the weight (A) of the PALATINOSE™ (isomaltulose) has a ratio of 20% or more relative to the total weight (B) of carbohydrate contained in the food material, and the PALATINOSE™ (isomaltulose) is combined so that the PALATINOSE™ (isomaltulose) is ingested by log or more per 60 kg of body weight of an individual.

Each of the above food material (7)-(12) or food processed from the food material can be ingested to reduce body fat accumulation resulted from the increase in blood glucose level and insulin secretion caused by ingesting the above foodstuff.

DESCRIPTION OF THE PREFERRED EMBODIMENTS

Figure 1:
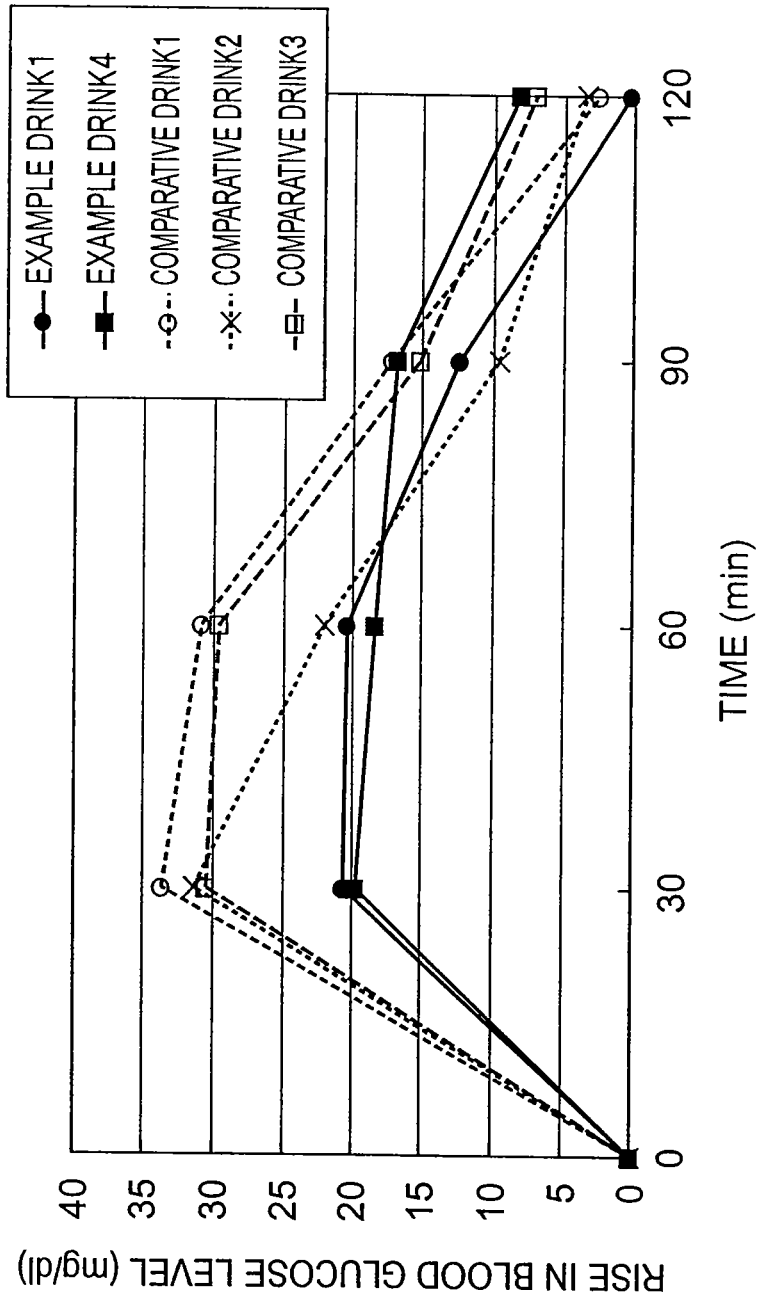
FIG. 1 is a diagram showing the changes in blood glucose level after ingesting drinks in Example 1.

The invention will be described below in details with respect to preferred embodiments.

Palatinose in the invention, which is also called as isomaltulose, is a disaccharide composed by allowing glucose to make an α-1,6-glucosyl bond to fructose.

Isomaltulose may be a hydrate. Monohydrate thereof has a melting point of 123-124° C., a specific rotation $[\alpha]^{20}_D$ of +97.2, a Fehling solution reduction of 52% relative to glucose, and a solubility of 38.4 g in 100 g water at 20° C. The aqueous solution tastes fine sweet and has about 40% in sweetness relative to sucrose.

Isomaltulose is naturally found in honey or sugarcane juice. It is also found in a product transferred from sucrose by the action of an α-glucosyltransferase (isomaltulose synthase) from bacteria or yeasts.

Isomaltulose is industrially manufactured by treating sucrose with an α-glucosyltransferase produced by a bacteria such as Protaminobacter rubrum and Serratia plymuthica.

In the invention, "a carbohydrate having an α-1,6-glucosyl bond ratio of from 0% to less than 50% relative to the total bonds among constituent saccharides" is classified into "a carbohydrate having no α-1,6-glucosyl bond" and "a carbohydrate having an α-1,6-glucosyl bond ratio of from above 0% to less than 50% relative to the total bonds among constituent saccharides."

Examples of "a carbohydrate having no α-1,6-glucosyl bond" include carbohydrates such as maltose, sucrose, high fructose corn syrup and glucose. Examples of "a carbohydrate having an α-1,6-glucosyl bond ratio of from above 0% to less than 50% relative to the total bonds among constituent saccharides" include starch, dextrin and branched dextrin. Isomaltose, panose, isopanose and isomaltotriose do not correspond to the carbohydrate causing the increase in blood glucose level in the invention, because they have an α-1,6-glucosyl bond ratio of 50% or more relative to the total bonds among constituent saccharides.

"A carbohydrate having an α-1,6-glucosyl bond ratio of from 0% to less than 50% relative to the total bonds among constituent saccharides" may be used alone or in combination of two or more. The carbohydrate includes not only a carbohydrate commercially available as a purified high-grade single component, but also a carbohydrate in a state contained in cereals such as wheat flour and potatoes. Wheat flour contains carbohydrate in a content of about 75%. About 98% of the carbohydrate is starch.

In the invention, "isomaltulose is ingested before or after or simultaneously with" means that PALATINOSE™ (isomaltulose) and one or more other carbohydrates are ingested during a meal or a between-meal snack. It does not always limitedly mean that they are mixed and ingested. Therefore, it includes ingesting a food or drink containing isomaltulose and one or more other carbohydrates which easily causes a blood glucose level increase. For example, a case where a drink containing isomaltulose is ingested before or after or simultaneously with consuming a cake or a cookie containing sucrose and starch corresponds to the condition: "isomaltulose is ingested before or after or simultaneously with" of the invention. More particularly, "isomaltulose is ingested before or after or simultaneously with" means a time range within which isomaltulose and one or more other carbohydrates can be mixed in stomach by consuming food at meal or between-meals when the isomaltulose stays in the stomach, or by ingesting isomaltulose when food at meal or between-meals stays in the stomach. The time range is generally from 30 minutes before consuming food to 2 hours after consuming the food, but varies depending on an individual, body condition or ingestion timing.

"Isomaltulose is ingested" includes ingesting isomaltulose alone and ingesting a food material containing isomaltulose, for example, a drink such as a refreshing drink, coffee and black tea, household dishes such as omelet and cooked dish, confectionery such as baked goods, pudding and bun with bean-jam filling, and breads including a sweet bun.

In the invention, "sweetener" is a substance to make food and drink sweet. It means a sweetener prepared for the purpose of coffee or black tea, or means a sweetener for use in household or business. The sweetener may be formed in powder, granule, a cube or liquid. It can be packaged in a stick, a small bag, a box or a portion.

"Premix material" means a foodstuff which is sold by previously mixing several materials containing isomaltulose and one or more other materials including a hot cake mix, a pound cake mix, a bread mix, a pancake mix, a steamed bread mix, a crepe mix, a cookie mix, a doughnut mix, a sponge cake mix, a jelly mix, a pudding mix, bean-jam with sugar and a dumpling powder.

"Powder drink" means a cocoa mix, coffee, a powdery juice, a powdered black tea, a powdered lemonade and an instant soup mix. It means a drink product which can be dissolved in a liquid such as hot water, water and milk to serve as a drink.

Among carbohydrates consumed before or after or simultaneous with isomaltulose, sucrose and high fructose corn syrup are sweetener. Therefore, the sweetness can be reduced by substituting a part of the sweetener with isomaltulose. Since consumers recently tend to like low sweet confectioneries and drinks, these products can be used as foods for such consumers. Alternatively, a highly sweet material such as high fructose corn syrup, fructose, aspartame, stevia sweetener or acesulfam K can be used together to adjust the product to a favorite sweetness. From the viewpoint of processing characteristics, isomaltulose in combination with sucrose prevent the food from coloring and prevent low soluble isomaltulose from crystallization, comparing with the case where isomaltulose is used alone.

It has been proved by the Examples as described below that isomaltulose, when ingested before or after or simultaneously with consuming a carbohydrate having an α-1,6-glucosyl bond ratio of from 0% to less than 50% relative to the total bonds among constituent saccharides such as sucrose, dextrin, starch and high fructose corn syrup, reduces an increase in blood glucose level caused by consuming the carbohydrate.

A group of ingesting 50 g of sucrose, a group of ingesting 25 g of sucrose and a group of ingesting 25 g of glucose, which were used as Comparative examples, showed a sudden increase in blood glucose level 30 minutes after the ingesting. As for cases where 50 g of sucrose and 25 g of glucose were ingested, respectively, the areas of a region surrounded by the blood glucose level increase curve and the baseline (area under blood glucose level increase curve) were nearly identical and high values. And as for the case where 25 g of sucrose was ingested, the values were slightly lower. Groups of ingesting 25 g of sucrose or 25 g of glucose in combination with 25 g of isomaltulose, which were measured as Examples, gave no sudden increases in blood glucose level after consuming these carbohydrates and gave significantly lower values in area under their blood glucose level increase curves comparing with the Comparative groups.

The area under blood glucose level increase curve after consuming 50 g of carbohydrate, which is a reference of Glycemic Index measurement, was measured for glucose and isomaltulose in combination of various ratios to obtain GI value thereof, which is expressed by a relative value taking the value measured after 50 g of glucose is ingested as 100%.

As a result, a curve showing decrease in the GI value according to increase in ratio of isomaltulose was obtained.

The result has revealed that isomaltulose, when ingested before or after or simultaneously with consuming glucose or sucrose, does not work additively in blood glucose level caused by the consumed glucose or sucrose, but reduces reversely the increase in blood glucose level caused by glucose and sucrose.

It has been also demonstrated that, since isomaltulose reduces the increase in blood glucose level caused by glucose and sucrose, the result is similarly true when high fructose corn syrup being nearly a sucrose decomposition product, and starch or dextrin being decomposed to form glucose, are replaced with sucrose or glucose.

As for a effect of reducing body fat accumulation, the previous report (New Food Industry, Vol. 31, No. 10, 9-15, (1989)) confirms that, when comparing a body fat accumulation amount between one rat group of providing a sucrose-containing feed as a high fat diet and another rat group of providing another feed in which all the sucrose was replaced by isomaltulose, the rat group provided with the feed containing isomaltulose showed a lower body fat accumulation amount. However, it was concluded that, comparing with values in body fat accumulation amount obtained by the sucrose-containing feed and the isomaltulose-containing feed, the value obtained by a feed in which a part of the sucrose was replaced by isomaltulose would be a value between above values depending on the ratio of added isomaltulose.

In the Example described later, three kinds of feeds were prepared, that is, a feed containing sucrose by 40% as a Comparative example, a isomaltulose feed in which all the sucrose was replaced with isomaltulose and a feed in which a part of the sucrose was replaced with isomaltulose. Each of these feeds was ingested by rats for a long period of time to compare degree of body fat accumulation. As a result, a group ingesting the isomaltulose feed showed a significantly lower value in fat tissue weight than a group ingesting the Comparative feed, as the conventional report on rat. But a group ingesting the feed in which a part of the sucrose was replaced with isomaltulose showed a significantly lower value in body fat accumulation amount than the group ingesting the feed as the Comparative example. Furthermore, The group showed a slightly lower value in fat tissue weight than the group ingesting the isomaltulose feed with a high effect to reduce body fat accumulation. Hence it has been demonstrated that the feed in which a part of sucrose is replaced with isomaltulose gives the same level of effect to reduce body fat accumulation as the feed in which all the sucrose is replaced with isomaltulose.

A reducer of blood glucose level increase or of body fat accumulation of the invention may contain isomaltulose as an active ingredient. It may contain isomaltulose alone or a mixture of isomaltulose with one or more other constituent components. Other constituent components include a pharmaceutically acceptable and publicly known ingredient or a carrier. In addition, It may include sucrose, wheat flour, starch, dextrin, and high fructose corn syrup as described above.

When the reducer of blood glucose level increase or of the body fat accumulation contains one or more other constituent components, they can have an optionally determined ratio between the reducer of blood glucose level or the reducer of body fat accumulation and one or more other constituent components depending on an ingestion amount and timing. The typical ratio of the reducer of blood glucose level increase : one or more other constituent components is 99.99: 0.01-10.00:90.00, preferably 99.99:0.01-20.00:80.00, and more preferably 99.99:0.01-30.00:70.00. The ratio of reducer of the body fat accumulation: the other constituent component is 99.99:0.01-20.00:80.00, preferably 99.99:0.01-30.00: 70.00, and more preferably 99.99:0.01-40.00:60.00.

When the weight of isomaltulose and the total weight of carbohydrate in a food material are designated by A and B respectively, the food material of the invention for reducing blood glucose level increase has an A/B ratio of 10% or more, and is preferably combined with isomaltulose to give an intake of 5 g or more per 60 kg of body weight of an individual. The A/B ratio of 20% or more is preferable, and 30% or more is more preferable. The isomaltulose is preferably incorporated to give an intake of log or more, more preferably 15 g or more per 60 kg of body weight of an individual.

When the weight of isomaltulose and the total weight of carbohydrate in a food material are designated by A and B respectively, the food material of the invention for reducing body fat accumulation has an A/B ratio of 20% or more, and isomaltulose is preferably combined to give an intake of log or more per 60 kg of body weight of an individual. The A/B ratio of 30% or more is preferable, and 40% or more is more preferable. The isomaltulose is preferably combined to give an intake of 15 g or more, more preferably 20 g or more per 60 kg of body weight of an individual.

Isomaltulose can be obtained by the method as described above. When it is applied to a reducer of blood glucose level increase or a reducer of body fat accumulation with one or more other constituent components, they can be prepared by a publicly known mixing or formulating method. An individual for the reducer of blood glucose level increase, the reducer of body fat accumulation and the food material of the invention may be human and a non-human animal (particularly a mammal). Oral ingestion can be used for an ingesting method.

EXAMPLE

The invention will be described below in more detail with reference to Examples, but is not limited to them.

Example 1

50 g of sucrose, 25 g of sucrose and 25 g of glucose were each dissolved in distilled water to get a total weight of 190 g to prepare the drink (Comparative drink 1, Comparative drink 2 and Comparative drink 3, respectively). Using each of the Comparative drinks as a control sample, a blood glucose level test after ingesting the drink was performed as will be described later. On the other hand, a combination of 25 g of sucrose and 25 g of isomaltulose, a combination of 42.5 g of glucose and 7.5 g of isomaltulose, a combination of 35 g of glucose and 15 g of isomaltulose, a combination of 25 g of glucose and 25 g of isomaltulose, and a combination of 25 g of glucose and 2.78 g of isomaltulose were each dissolved in distilled water to get a total weight of 190 g to prepare the drink (Example drink 1, Example drink 2, Example drink 3, Example drink 4 and Example drink 5, respectively). Using each of the Example drinks as a test sample, a blood glucose level test after ingesting the drink was performed.

The blood glucose level test was as follows: Five healthy volunteers (4 males and 1 female), 31-40 aged, were selected as the test subjects. They took no breakfast on a test day and kept fasting for 12 hrs or more before the start of the test. Their bloods were collected before ingesting a drink (0 min), and 30 min, 60 min, 90 min, and 120 min after ingesting it. As a result their blood glucose levels are determined. One kind of drink was ingested for one test. Another drink was ingested on another day and the test was carried out once a day for total 8 days. The same five test subjects were applied to all the tests for blood glucose levels. In the Example 1, the free style Kissei kit (made by Kissei Pharmaceutical Co., LTD) was used to collect blood samples and test a blood glucose level.

The blood glucose level increase curves are shown in FIG. 1 to compare the changes in blood glucose level after ingesting each of the drinks. FIG. 1 reveals that a blood glucose level increase is reduced after the simultaneous ingestion of 25 g of isomaltulose and 25 g of glucose, compared with after the ingestion of 25 g of glucose alone. A blood glucose level increase is reduced after the simultaneous ingestion of 25 g of isomaltulose and 25 g of sucrose, compared with after the ingestion of 50 g of sucrose alone and 25 g of sucrose alone. Particularly, there is a remarkable difference between the Example drink and the Comparative drink as to a sudden increase in blood glucose level at 30 min after ingesting.

Figure 2:
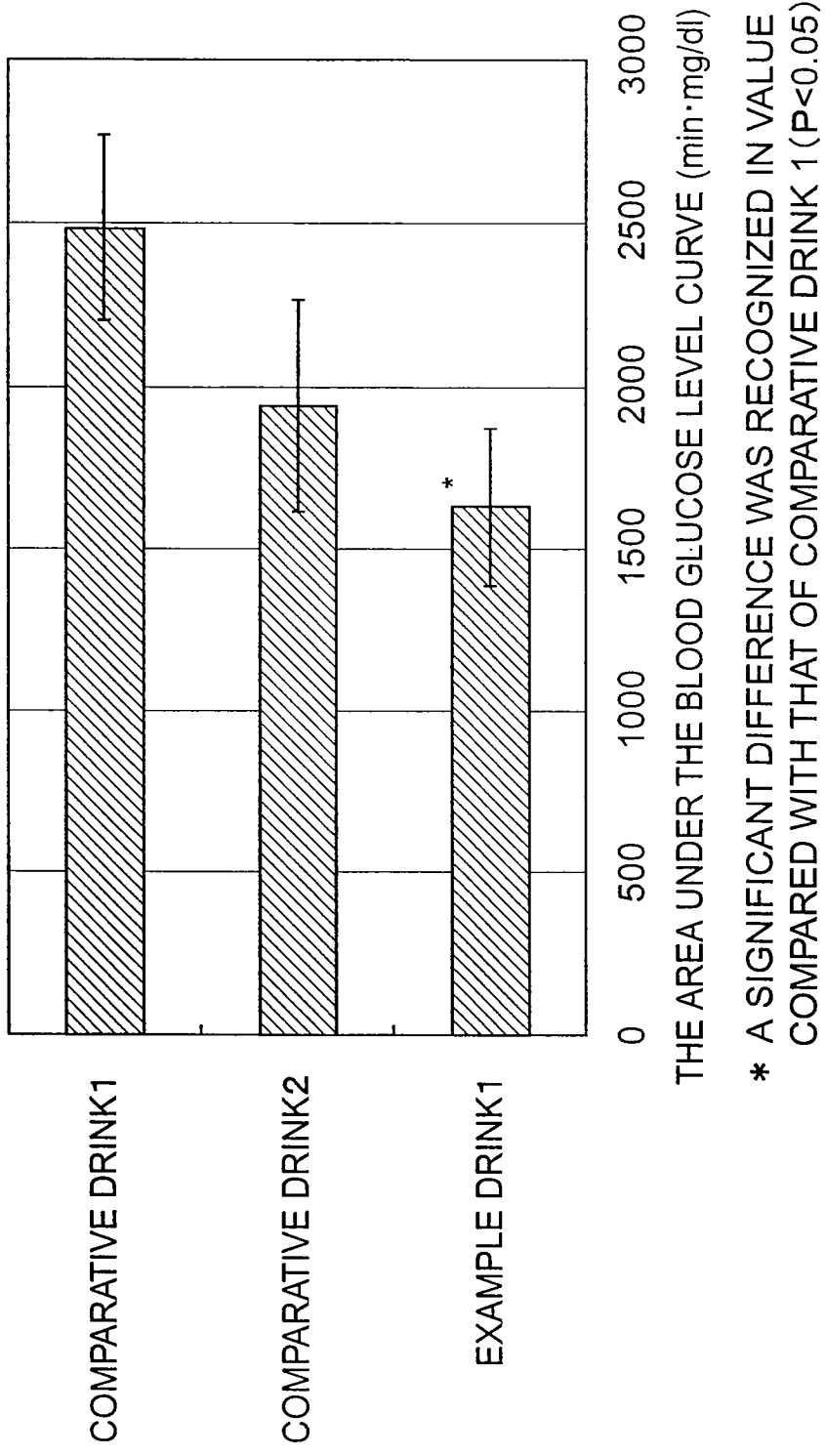
FIG. 2 is a diagram showing the areas under blood glucose level increase curve after ingesting sucrose-containing drinks in Example 1.

As shown in FIG. 2, the comparison in averages calculated from the area under blood glucose level increase curves of the each test subject for 120 min after ingestion of sucrose alone or the simultaneous ingestion of sucrose and isomaltulose is carried out. As a result, it is revealed that the area under blood glucose level increase curve for the simultaneous ingestion of 25 g of sucrose and 25 g of isomaltulose (Example drink 1) was significantly lower than that for the ingestion of 50 g of sucrose (Comparative drink 1) with a risk rate of less than 5%, though the both drinks had the same level in carbohydrate weight and energy amount. Further, ingestion of 25 g of the sucrose (Comparative drink 2) gave a higher value of area under blood glucose level increase curve than ingestion of Example drink 1, though Comparative drink 2 had a lower level in carbohydrate weight and calorie.

Figure 3:
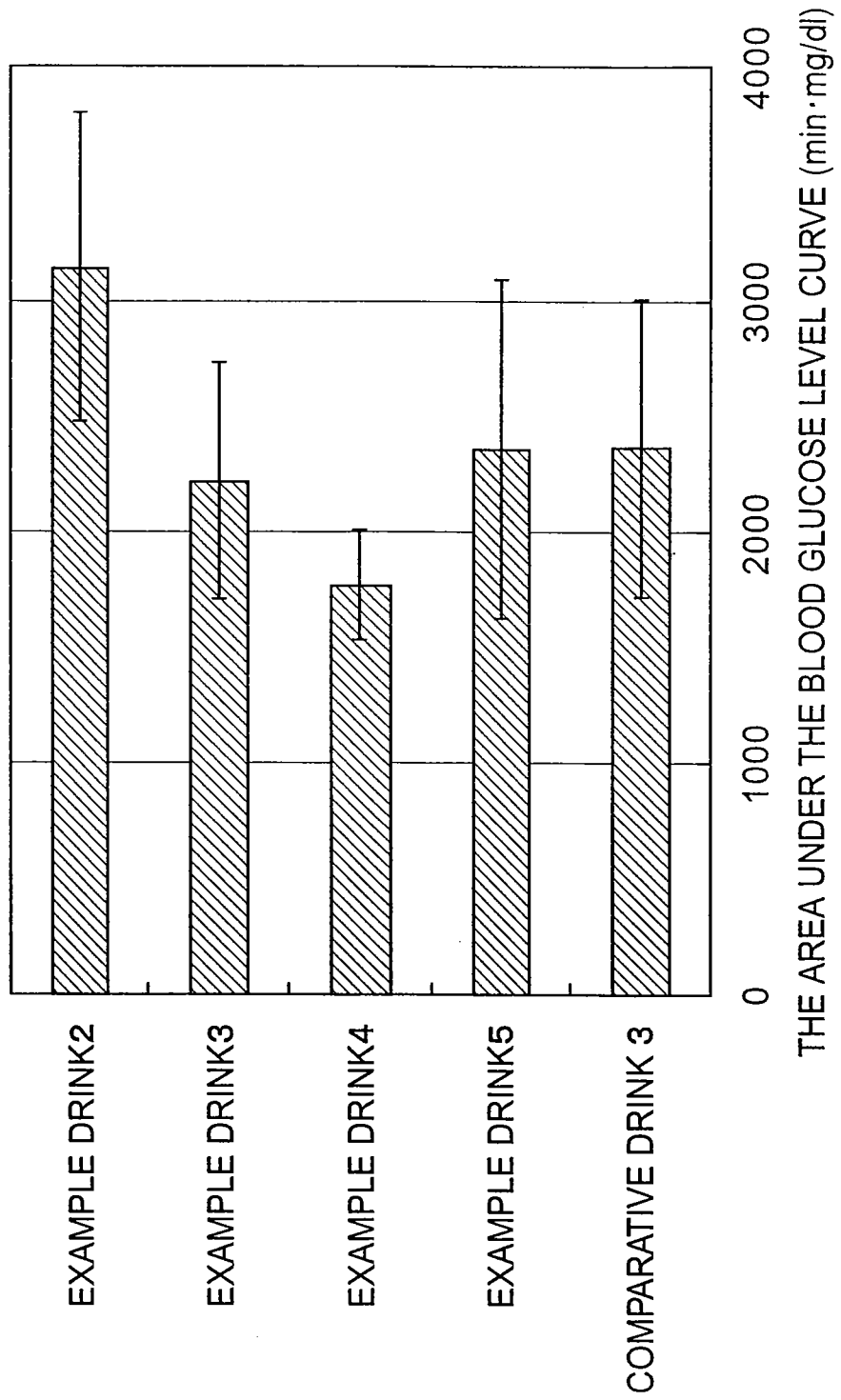
FIG. 3 is a diagram showing the areas under blood glucose level increase curve after ingesting glucose-containing drinks in Example 1.

FIG. 3 shows the effect when glucose and isomaltulose are ingested together. In the drinks having a constant carbohydrate weight of 50 g (Example drinks 2, 3 and 4), the area under blood glucose level increase curve decreased according to the increase of the ratio of isomaltulose. Further, in the drinks having a constant glucose weight of 25 g (Comparative drink 3, Example drinks 4 and 5), the area under blood glucose level increase curve decreased according to the increase of isomaltulose amount ingested simultaneously, though the consumed carbohydrate amount increased.

Figure 4:
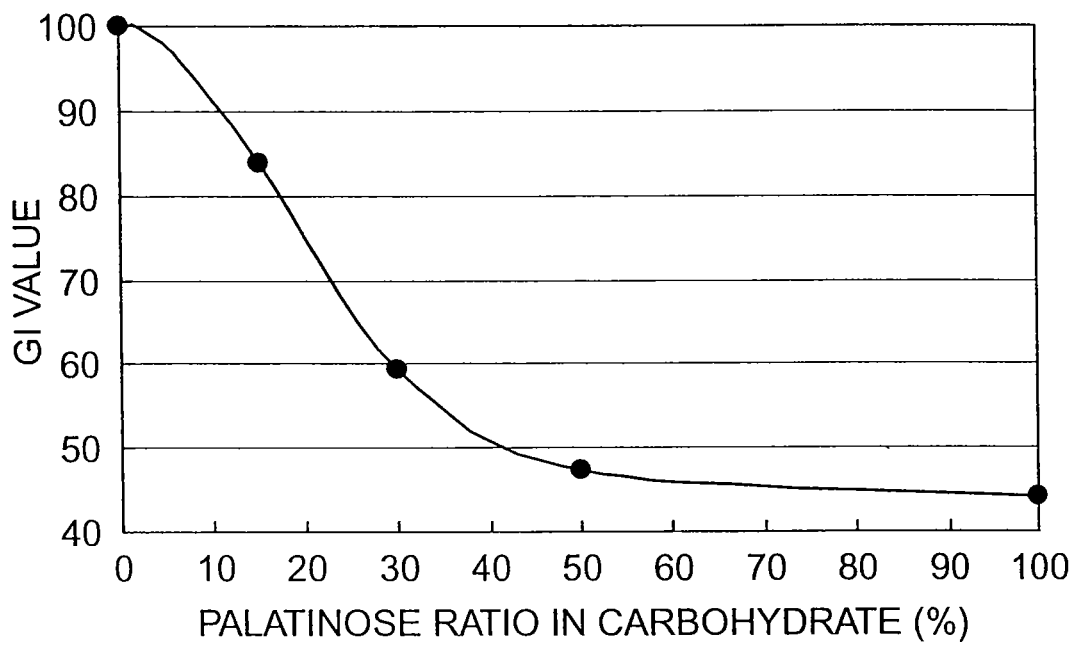
FIG. 4 is a diagram showing the relation between PALATINOSE™ (isomaltulose) percent in carbohydrate and GI value, wherein the carbohydrate is consumed by a weight of 50 g.

FIG. 4 shows a graph for plotting GI values versus isomaltulose ratio in the consumed carbohydrate (total 50 g) as the horizontal axis using the thus obtained data, the isomaltulose GI value (isomaltulose 100%) and the glucose GI value (isomaltulose 0%). This reveals that the GI value decreased according to the increase of the isomaltulose ratio though the same carbohydrate amount and energy amount were ingested. Particularly when the isomaltulose ratio went beyond 50%, the GI value went below 50 and felled to a value nearly equal to the value when 100% of isomaltulose (50 g) was ingested. Further, FIG. 4 indicates that the GI value surely decreased when a isomaltulose ratio in a total carbohydrate (the total weight 50 g) was 10% or more.

However, the GI value after ingesting of Example drink 5 (containing glucose 25 g and isomaltulose 2.78 g) was insignificantly lower than that of Comparative drink 3 (glucose 25 g), though the Example drink 5 had a isomaltulose ratio of 10% in the total carbohydrate. This teaches that there exists the minimum intake of isomaltulose necessary for the isomaltulose effect in addition to the isomaltulose ratio in the consumed carbohydrate. The result of the Example indicates that the minimum intake of isomaltulose necessary to reduce an increase in blood glucose level is 5 g or more.

The above result reveals that the simultaneous use of sucrose or glucose with isomaltulose has an effect for reducing an increase in blood glucose level.

Example 2

20 g of isomaltulose was dissolved in distilled water to make a total weight of 190 g to prepare an Example drink. 190 g of distilled water was used as a Control drink. The both drinks were used as the test samples for a blood glucose level test as described below.

The blood glucose level test was as follows. Seven healthy volunteers (5 males and 2 females), 31-55 aged, were selected as the test subjects. They took breakfast by the time of 4 hours before determining a blood glucose level and the blood glucose level prior to the drink ingestion was measured. The Example drink (190 g) or the Control drink (190 g) was ingested while ingesting a packed lunch (trade name: Nidan Orizume Makunouchi, made by Warabeya Nichiyo KK, energy: 718 Kcal, protein: 29.8 g, fat: 20.0 g, carbohydrate: 104.6 g, and sodium: 1.4 g). The test subjects' blood was collected with time 30 min, 60 min, 90 min and 120 min after the meal to measure their blood glucose levels. One kind of drink was ingested for one test. The other drink was ingested on another day and the test was carried out once a day for total 2 days. Accordingly, one test subject was tested twice for blood glucose level, that is, after ingesting the Example drink and after ingesting the Control drink. The free style Kissei kit (made by Kissei Pharmaceutical Co., LTD) was used to collect blood and to measure blood glucose level, as Example 1.

Figure 5:
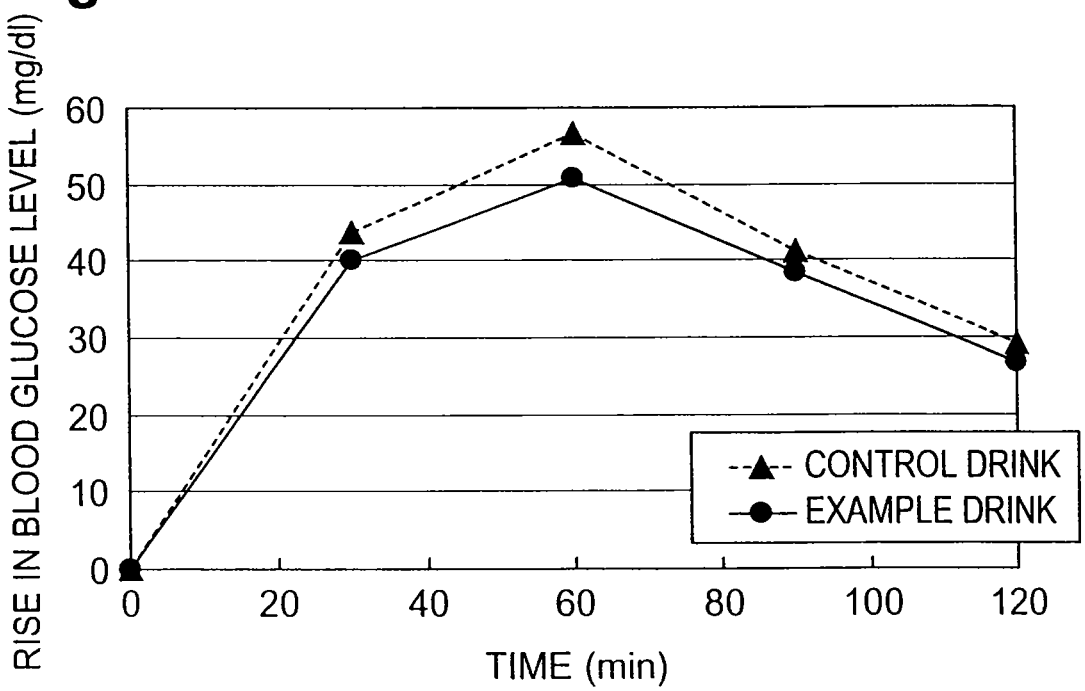
FIG. 5 is a diagram showing the changes in blood glucose level after ingesting drinks in Example 2.
Figure 6:
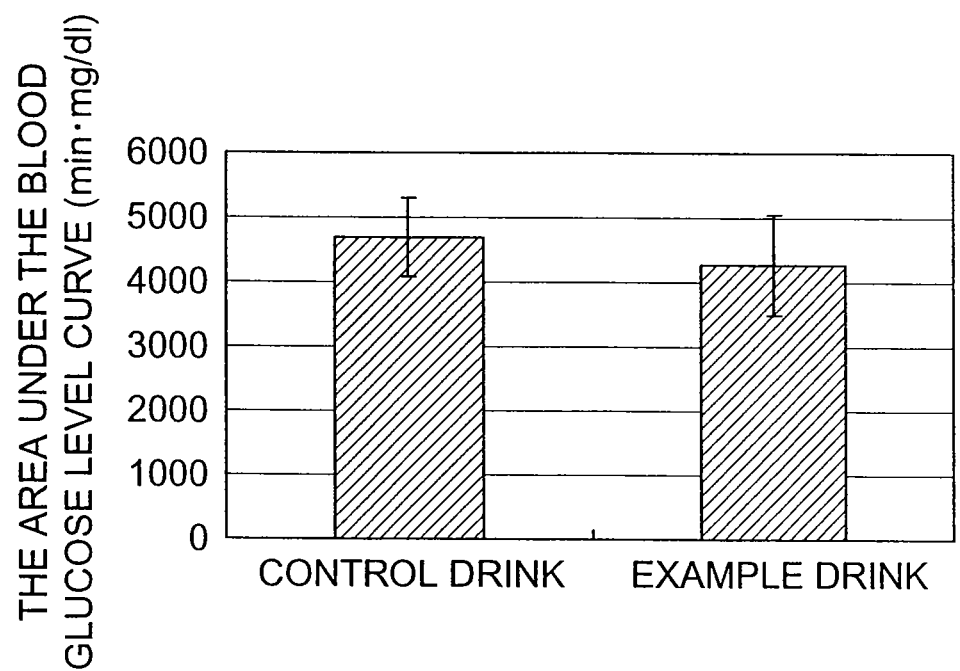
FIG. 6 is a diagram showing the areas under blood glucose level increase curve after ingesting drinks in Example 2.

The blood glucose level increase curves are shown in FIG. 5 to compare the changes in blood glucose level after ingesting the respective drinks. FIG. 5 reveals that the increase in blood glucose level after ingesting the Example drink (isomaltulose) was slower than that after ingesting the Control drink (distilled water). The areas under blood glucose level curves are shown in FIG. 6. The graph reveals that the value of the area under blood glucose level curve of the case where the Example drink was ingested simultaneously with consuming food was lower compared with that of the case where the Control drink was ingested simultaneously with consuming food.

The above result reveals that isomaltulose ingested simultaneously with consuming food can reduce a blood glucose level increase after consuming the food.

Example 3

Mice were consecutively fed with a feed added with isomaltulose, a feed added with sucrose and no isomaltulose, and a feed added with both isomaltulose and sucrose to compare their body fat accumulation amount.

C57BL/6CrSlc(SPF) male mice (30 heads) aged 7 weeks were fed with a commercial powder feed (trade name: CRF-1 powder, made by Oriental Yeast Co., LTD) and water ad libitum to prefeed for a week. Then, they were separated into three groups each including 10 heads, that is, a group of feeding with a feed (Comparative feed) containing sucrose by 66.7% in carbohydrate, a group of feeding with a feed (Example feed 1) containing isomaltulose by 66.7% in carbohydrate, and a group of feeding with a feed (Example feed 2) containing isomaltulose by 30.0% and sucrose by 36.7% in carbohydrate. The groups were fed with their respective feeds and water ad libitum for 8 weeks. Detailed composition of each feed is shown in Table 1. The feeding condition was as follows: temperature 22±3° C., humidity (relative humidity) 50±20%, ventilation cycles 13-17 times/hr, and lighting time 8:00-20:00 (light 12 hrs, dark 12 hrs).

TABLE 1

|  | Comparative feed | Example feed 1 | Example feed 2 |
| --- | --- | --- | --- |
| corn starch | 14.95 | 14.95 | 14.95 |
| sucrose (granulated sugar) | 40.00 | 0.00 | 22.00 |
| isomaltulose | 0.00 | 40.00 | 18.00 |
| cellulose | 5.00 | 5.00 | 5.00 |
| soybean oil | 15.00 | 15.00 | 15.00 |
| mineral (AIN-93mineral mix) | 3.50 | 3.50 | 3.50 |
| vitamin (AIN-93vitamine mix) | 1.00 | 1.00 | 1.00 |
| L-cystine | 0.30 | 0.30 | 0.30 |
| choline bitartarate | 0.25 | 0.25 | 0.25 |
| casein | 20.00 | 20.00 | 20.00 |

After the end of the feeding, the mice were light anesthetized with ether and sectioned abdominally to exsanguinate from postcava to death. For a typical example of every group, digital photographs showing body fat accumulation inside the abdominal cavity were taken. Then, for all the cases, the kidney peripheral fat (including the retroperitoneal fat) and the epididymis peripheral fat were taken out to measure their wet weights separately in left and right. The mesenteric fat also was taken out to measure its wet weight. These three kinds of fat tissues are typical of visceral fat. The data were statistically treated to ascertain the homoscedasticity and further to carry out the t-test, which is of correspondency, in the case of homoscedasticity.

Figure 7:
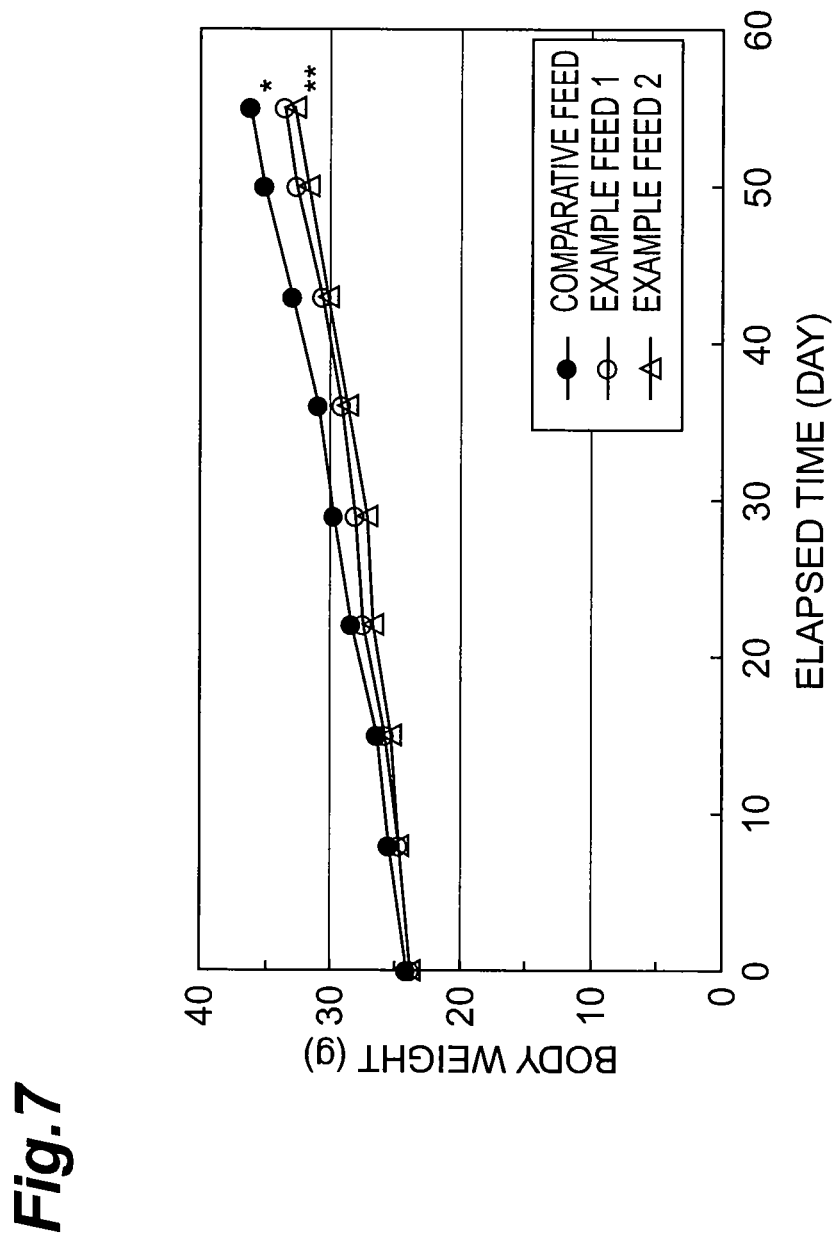
FIG. 7 is a diagram showing the transition in body weight after ingesting feeds in Example 3.
Figure 8:
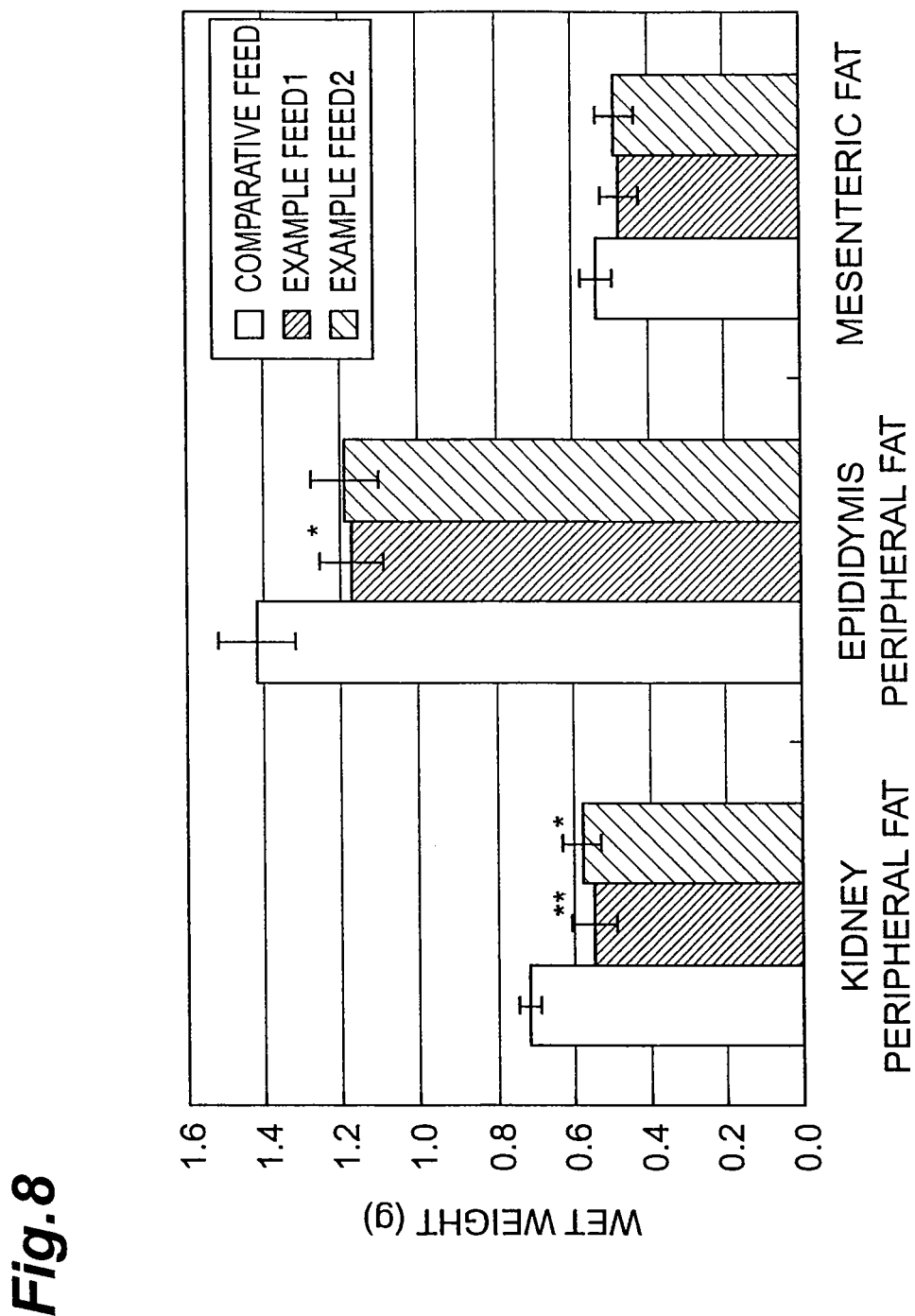
FIG. 8 is a diagram showing the wet weights of different fat tissues after ingesting feeds in Example 3.
Figure 9:
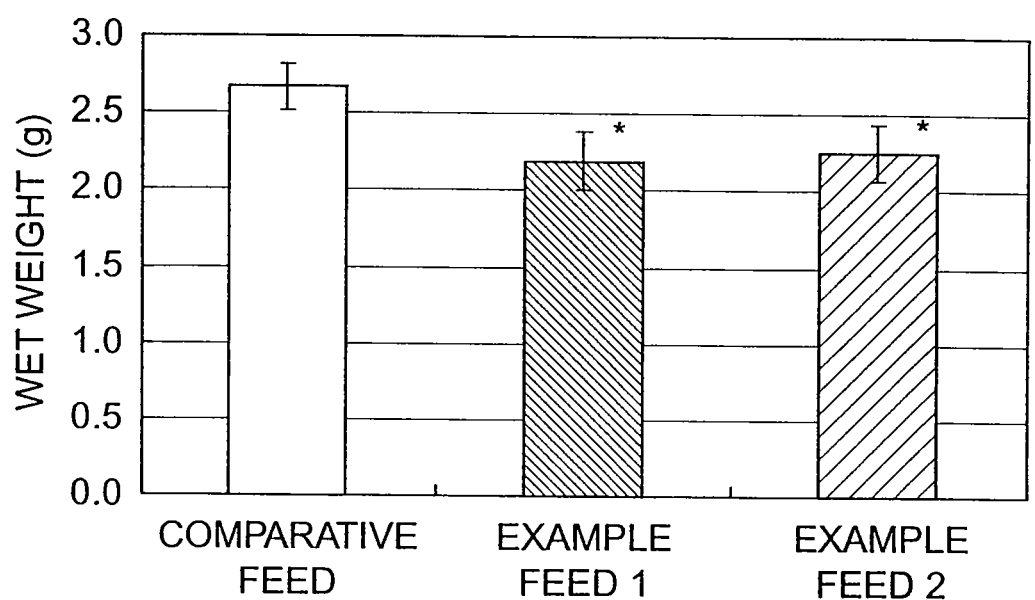
FIG. 9 is a diagram showing the sum of the wet weights of different fat tissues in FIG. 8.

The changes in body weight of respective groups are shown in FIG. 7. Body weights of the mice fed with the Example feeds were significantly lower than those of the mice fed with the Comparative feed. As shown in FIG. 8, comparing the fat tissue weights measured after feeding, the mice fed with the Example feed showed lower value of kidney peripheral fat and epididymis peripheral fat compared with the mice fed with the Comparative feed. As shown in FIG. 9, comparing the summed values of weight of kidney peripheral fat, epididymis peripheral fat and mesentery fat as the total visceral fat weight, the mice fed with the Example feeds showed a significantly lower value compared with the mice fed with the comparative feed.

The above results indicate that a feed added with isomaltulose as carbohydrate can reduce the rise in body weight and the accumulation in body fat compared with a feed added with sucrose as carbohydrate when mice consecutively ingest these feed, respectively.

Transition in the rise of body weight and state of the body fat accumulation were nearly equal in the case where the Example feed 1 with 40% isomaltulose was ingested and the case where the Example feed 2 with 22% sucrose and 18% isomaltulose was ingested, and the case where the Example feed 2 was ingested showed a slightly lower value. Accordingly, it has been revealed that a feed containing both isomaltulose and sucrose exerts effects of reducing the increase in body weight and the accumulation of body fat as well as a feed containing isomaltulose alone. Since the additive amount of sucrose was larger than that of isomaltulose in Example feed 2, the isomaltulose contained in the feed may exert the effect of reducing the accumulation of body fat caused by ingesting the sucrose.

The result of this Example demonstrates that isomaltulose exerts the effect of reducing the accumulation of body fat when it is contained at a ratio of 20% or more in carbohydrate.

The minimum intake of isomaltulose necessary to reduce a body fat accumulation is presumed to be 10 g or more in terms of an intake ingested by a person having a body weight of 60 kg.

Example 4

[Stick Sugar Containing Isomaltulose and Sucrose]

Isomaltulose and sucrose were mixed at identical weights, and packed in a stick package by 3.5 g respectively per one package. The stick sugar thus obtained is a food material containing isomaltulose and sucrose for reducing a blood glucose level increase.

Example 5

[Gum Syrup Containing Isomaltulose and High Fructose Corn Syrup]

Gum syrup containing isomaltulose and high fructose corn syrup with the composition as shown in Table 2 below was prepared. The isomaltulose and gum arabic were joined and powdery mixed, to which the high fructose corn syrup and water were added, then boiled and mixed. The solution thus obtained was adjusted to 30 using a refractometer/Brix meter.

TABLE 2

| component | g |
|---|---|
| crystalline isomaltulose (Trade name: Crystalline palatinose-IC, made by Shin Mitsui Sugar Co., LTD.) | 27.0 |
| high fructose corn syrup (fructose glucose liquid sugar) (Trade name: EP-O, made by San-ei Sucrochemical Co., LTD., 75%) | 48.0 |
| gum arabic | 4.0 |
| water | 200.0 |

Example 6

[Tablet Containing Isomaltulose and Sucrose]

A tablet containing isomaltulose and sucrose with the composition as shown in Table 3 below was prepared. The mixed powder with the following composition was compressed at a tableting pressure of 300 kg/cm$^3$ to make a 18 mm diametric, 5 mm thick, and 1.5 g weighing tablet.

TABLE 3

| component | compounding ratio (weight) |
|---|---|
| pulverized isomaltulose (obtained by pulverizing crystalline isomaltulose (Trade name: Crystalline palatinose-IC, made by Shin Mitsui Sugar Co., LTD.) by an atomizer) | 27.5 |
| powder sugar | 27.5 |
| citric acid | 1 |
| sugar ester | 1 |
| Aspartame | 0.05 |
| vitamin P | 0.0002 |
| water | 0.6 |
| lemon juice | proper quantity |

Example 7

[Powder Drink Containing Isomaltulose and Sucrose]

A powder drink containing isomaltulose and sucrose with the composition as shown in Table 4 below was prepared by a conventional method using a universal mixing stirrer.

TABLE 4

| component | compounding ratio (weight) |
|---|---|
| crystalline isomaltulose (Trade name: Crystalline palatinose-IC, made by Shin Mitsui Sugar Co., LTD.) | 42.35 |
| sucrose (granulated sugar) | 42.35 |
| powder juice | 10 |
| anhydrous citric acid | 3 |
| sodium citrate | 0.4 |
| L-ascorbic acid | 0.5 |
| sodium ascorbate | 0.3 |
| riboflavin (content 10% by weight) | 0.1 |

Example 8

[Refreshing Drink Containing Isomaltulose and Sucrose]

A refreshing drink containing isomaltulose and sucrose with the composition as shown in Table 5 below was prepared. The raw materials were dissolved in 250 ml of boiling hot water to fill in a drink can (for 250 ml).

TABLE 5

| component | g/can |
|---|---|
| crystalline isomaltulose (Trade name: Crystalline palatinose-IC, made by Shin Mitsui Sugar Co., LTD.) | 4 |
| sucrose (granulated sugar) | 4 |
| citric acid | 0.15 |
| vitamin C | 0.03 |
| sodium chloride | 0.05 |
| potassium chloride | 0.04 |
| calcium chloride | 0.012 |
| magnesium carbonate | 0.002 |
| sodium glutamate | 0.006 |
| stevia sweetener | 0.01 |
| vitamin P | 0.0004 |
| flavoring agent | proper quantity |

Example 9

[Sponge Cake Containing Isomaltulose, Sucrose and Starch]

A sponge cake containing isomaltulose, sucrose and starch with the composition as shown in Table 6 below was prepared. Crystalline isomaltulose, sucrose (granulated sugar) and xanthan gum were powdery mixed to make a mixture called A. Wheat flour and baking powder were mixed to make a mixture called B. Milk and the Ryoto ester SP were added to A and mixed thoroughly, followed by adding egg and thorough mixing to become homogeneous, which was warmed up to about 25° C. in hot bath. This mixture was bubbled up by a universal stirrer until no more bubble could be generated. The resultant was mixed, with B to make a mixture without kneading B, The mixture was filled in a sponge cake tin to bake in an oven at 160° C. for 40 min. The composition of this Example contained 70 g of isomaltulose, 30 g of sucrose and about 90 g of starch.

TABLE 6

| component | g |
|---|---|
| egg | 200 |
| isomaltulose powder sugar (Trade name: powder palatinose-ICP, made by Shin Mitsui Sugar Co., LTD.) | 70 |
| sucrose (granulated sugar) | 30 |

TABLE 6-continued

| component | g |
|---|---|
| wheat flour | 120 |
| milk | 41 |
| xanthan gum | 0.6 |
| foaming agent (Trade name: Ryoto Ester SP, made by Mitsubishi-Kagaku Foods Corporation) | 9.2 |
| baking powder | 3 |

Example 10

[Refreshing Drink Containing Isomaltulose and High Fructose Corn Syrup]

A refreshing drink containing isomaltulose and high fructose corn syrup with the composition as shown in Table 7 below was prepared. The raw materials were dissolved in 250 ml of hot water to fill in a drink can (for 250 ml).

TABLE 7

| component | g/can |
|---|---|
| crystalline isomaltulose (Trade name: Crystalline palatinose-IC, made by Shin Mitsui Sugar Co., LTD.) | 4 |
| high fructose corn syrup | 5.33 |
| citric acid | 0.15 |
| vitamin C | 0.03 |
| sodium chloride | 0.05 |
| potassium chloride | 0.04 |
| calcium chloride | 0.012 |
| magnesium carbonate | 0.002 |
| sodium glutamate | 0.006 |
| stevia sweetener | 0.01 |
| vitamin P | 0.0004 |
| flavoring agent | proper quantity |

Example 11

[Madeleine Containing Isomaltulose and Starch]

A madeleine containing isomaltulose and starch with the composition as shown in Table 8 below was prepared. Wheat flour and baking powder had been mixed and sieved. Butter had been melted in a hot bath. Egg was fed in a ball, to which granulated sugar, kitchen salt, lemon peel and lemon essence were added followed by warming in a hot bath. While warming, isomaltulose was fed in, and the mixture was stirred thoroughly by a eggbeater. The sieved wheat flour was added at a bulk to be mixed thoroughly and then the melted butter was added to be mixed. The resultant was separated to fill into aluminum foil cups and baked in an oven at 160° C. for about 10 min until browned. The madeleine prepared by the Example contained 60 g of isomaltulose and about 37 g of starch.

TABLE 8

| component | g |
|---|---|
| wheat flour (soft flour) | 50 |
| baking powder | 1 |
| butter | 40 |
| egg | 60 |
| crystalline isomaltulose (Trade name: Crystalline palatinose-IC, made by Shin Mitsui Sugar Co., LTD.) | 60 |
| kitchen salt | 0.2 |

TABLE 8-continued

| component | g |
|---|---|
| grated lemon peel | proper quantity |
| lemon essence | proper quantity |

Example 12

[Cake Mix Containing Palatines, Sucrose and Wheat Flour]

A cake mix with the composition as shown in Table 9 below was prepared. Materials excluding shortening were previously mixed and then the molten shortening was added and mixed to be sieved.

TABLE 9

| component | compounding ratio (weight) |
|---|---|
| wheat flour (soft flour) | 33.0 |
| isomaltulose powder sugar (Trade name: powder palatinose-ICP, made by Shin Mitsui Sugar Co., LTD.) | 25.0 |
| granulated sugar | 9.6 |
| sodium bicarbonate | 0.6 |
| sodium pyrophosphate | 1.0 |
| shortening | 25.0 |
| skim milk powder | 5.0 |
| flavoring agent | 0.2 |
| emulsifying agent (Trade name: Ryoto Sugar Ester S-1170, made by Mitsubishi-Kagaku Foods Corporation) | 0.1 |
| kitchen salt | 0.5 |

Example 13

[Hot Cake Mix Containing Isomaltulose and Wheat Flour]

A hot cake mix was prepared by powdery mixing raw materials with the composition as shown in Table 10 below. Materials excluding shortening were previously mixed and then the molten shortening was added and mixed to be sieved.

TABLE 10

| component | compounding ratio (weight) |
|---|---|
| wheat flour (soft flour) | 63.0 |
| powder isomaltulose (Trade name: powder palatinose-ICP, made by Shin Mitsui Sugar Co., LTD.) | 23.0 |
| baking powder | 3.5 |
| skim milk powder | 6.0 |
| flavoring agent | 0.2 |
| kitchen salt | 0.1 |
| emulsifying agent (Trade name: Ryoto Sugar Ester S-1170, made by Mitsubishi-Kagaku Foods Corporation) | 0.1 |
| xanthan gum | 0.1 |
| shortening | 4.0 |

Test Example 1

A combination of sucrose and isomaltulose was ascertained to be more resistant to color than isomaltulose alone.

5 g of carbohydrate and 1 g of glutamic acid were dissolved in distilled water to prepare a sample having a total weight of 50 g. Three kinds of samples were prepared, that is, a sample containing sucrose alone as the carbohydrate, a sample containing isomaltulose alone as the carbohydrate, and a sample containing a combination of 2.5 g sucrose and 2.5 g isomaltulose as the carbohydrate. These samples were filled in 100 ml capped vials and then heated at 100° C. for 50 min. After the heating, samples were cooled and respective absorbances were measured at a wavelength of 420 nm. As a result, the sample containing isomaltulose alone as the carbohydrate gave an absorbance of 0.004, and the sample containing sucrose alone gave that of 0.0015, while the sample containing isomaltulose and sucrose by the equal weight gave that of 0.002. The sample containing isomaltulose and sucrose by the equal weight was more suppressed from coloring than the sample containing isomaltulose alone. This absorbance by the isomaltulose was a value which allowed a user to visually recognize the sample to be colored brown.

Three same kinds of samples were prepared and treated in an autoclave at 121° C. for 20 min, that is, the same level as in retort sterilization for a canned food, and measured the absorbance at a wavelength of 420 nm. As a result, the sample containing isomaltulose alone as the carbohydrate gave an absorbance of 0.322, and the sample containing sucrose alone gave that of 0.020, while the sample containing isomaltulose and sucrose by the equal weight gave that of 0.069. The sample containing isomaltulose and sucrose by the equal weight was clearly more suppressed from coloring than the sample containing isomaltulose alone. All the samples were visually colored brown. But the sample containing isomaltulose alone as the carbohydrate had clearly deep brown, while the sample containing sucrose alone and the sample containing both isomaltulose and sucrose had clearly light brown.

It has been concluded from the above result that use of a combination of isomaltulose and sucrose in a processed food can not only reduce an increase in blood glucose level caused by the sucrose, but also suppress a heat coloring caused by the isomaltulose, comparing with use of isomaltulose alone.

Test Example 2

[Suppression of Crystallization by Simultaneous use of Isomaltulose and Sucrose]

A combination of isomaltulose and sucrose was ascertained to be more resistant to crystallize than isomaltulose alone.

A solution containing 50 wt % of sucrose, a solution containing 50 wt % of isomaltulose, and a solution containing each 25 wt % of sucrose and isomaltulose were prepared by 100 ml respectively, and then they were filled in capped screw vials. Dissolution was performed until no crystal remained at 50° C. These vials were put in a refrigerator set at 5° C. to observe crystallization.

After 2 days of storage, the solution containing isomaltulose alone began crystallization, and after 6 days amount of the crystal was measured. 10.77 g of isomaltulose was demonstrated to have crystallized. As for the solution containing sucrose alone and the solution containing both sucrose and isomaltulose, no crystallization were observed during the days.

The above result reveals that isomaltulose contained in a concentration where it tends to crystallize when used alone dose not crystallize when it is simultaneously used with sucrose.

By ingesting isomaltulose before or after or simultaneously with consuming a kind of carbohydrate such as sucrose, glucose and high fructose corn syrup, which has an α-1,6-glucosyl bond ratio of from 0% to less than 50% relative to the total bonds among constituent saccharides, an increase in blood glucose level caused by the carbohydrate can be reduced. Furthermore, isomaltulose, when used as a raw material in combination with one or more other carbohydrates such as nonreducing sugar, can reduce a factor for coloring to make food resistant to coloring and, when used in a combination with one or more other carbohydrates with high solubility, becomes not to tend to crystallize.

Isomaltulose, when used in combination with a sweetener such as sucrose and high fructose corn syrup, reduces the sweetness caused by the sucrose, glucose or high fructose corn syrup, resulting in providing food with low sweetness.

When an effect of reducing an increase in blood glucose level is exerted by ingesting isomaltulose before or after or simultaneously with consuming one or more other carbohydrates, or consuming food containing a combination of isomaltulose and one or more other carbohydrates in the raw material, insulin secretion is also reduced to result in exerting an effect of reducing a body fat accumulation. The invention can be applied to not only human but also a non-human animal (particularly a mammal).

What is claimed is:

1. A method for reducing blood glucose level increase in a human caused by consuming a carbohydrate selected from the group consisting of glucose, sucrose, high fructose corn syrup, starch, and dextrin, the method comprising the steps of:
   (a) providing isomaltulose as a reducer of blood glucose level increase;
   (b) having a human individual ingest the isomaltulose separately up to 30 minutes before consuming the carbohydrate, or simultaneously with consuming the carbohydrate, or separately after consuming the carbohydrate within a time range within which the isomaltulose and carbohydrate can be mixed in the stomach, in an amount of 5 g or more per 60 Kg of body weight of the human individual, and
   (c) selecting a time and amount of isomaltulose ingestion to reduce the increase in the human individual's blood glucose level in response to ingesting the isomaltulose compared to the increase in the human individual's blood glucose level absent the human individual ingesting the isomaltulose,
   wherein the weight of the isomaltulose has a ratio of from 10% to 50% relative to the total weight of the carbohydrate.

2. A method for reducing a blood glucose level increase in a human caused by consuming a carbohydrate, the method comprising the steps of:
   (a) providing a reducer of blood glucose level increase, wherein the reducer comprises isomaltulose as an active ingredient;
   (b) having a human individual ingest the reducer of blood glucose level increase;
   (c) having a human individual consume the carbohydrate, wherein the reducer is ingested separately up to 30 minutes before consuming the carbohydrate, or simultaneously with consuming the carbohydrate, or separately after consuming the carbohydrate within a time range within which the isomaltulose and carbohydrate can be mixed in the stomach, and wherein the carbohydrate has an α-1,6-glucosyl bond ratio of from 0% to less than 50% relative to the total bonds among constituent saccharides, wherein the carbohydrate includes a sufficient amount of glucose to increase blood glucose level in the human after consumption of the carbohydrate, and the isomaltulose is combined in the reducer so that the isomaltulose is ingested by the human individual in an amount of 5 g or more per 60 Kg of body weight of the human individual; and (d) selecting a time and amount of isomaltulose ingestion to reduce the increase in the human individual's blood glucose level in response to ingesting the isomaltulose compared to the increase in the human individual's blood glucose level absent the human individual ingesting the isomaltulose.

3. The method according to claim 2, wherein the weight of the isomaltulose has a ratio of 10% or more relative to the total weight of the carbohydrate.

4. The method according to claim 2, wherein the carbohydrate comprises at least one foodstuff selected from the group consisting of sucrose, wheat flour, starch, dextrin and high fructose corn syrup.

5. The method according to claim 1, wherein the reducer is in the form of a powder drink or a tablet.

6. The method according to claim 5, wherein the reducer is in the form of the powder drink, and the powder drink is selected from the group consisting of a cocoa mix, a coffee, a powdery juice, a powdered black tea, a powdered lemonade and an instant soup mix.

7. A method for reducing the blood glucose level increase in a human caused by consuming food, the method comprising the steps of:
(a) providing a reducer of blood glucose level increase, wherein the reducer comprises isomaltulose as an active ingredient;
(b) having a human individual ingest the reducer of blood glucose level increase;
(c) having the human individual consume a food comprising a carbohydrate, wherein the reducer is ingested separately up to 30 minutes before consuming the food, or simultaneously with consuming the food, or separately after consuming the food within a time range within which the isomaltulose and carbohydrate can be mixed in the stomach, and wherein the carbohydrate has an $\alpha$-1,6-glucosyl bond ratio of from 0% to less than 50% relative to the total bonds among constituent saccharides, and wherein the food consumed includes 50 g to 150 g of the carbohydrate,
wherein the weight of the isomaltulose has a ratio of 10% or more relative to the total weight of the carbohydrate, and the isomaltulose is combined in the reducer so that the isomaltulose is ingested by the human individual in a dosed amount of 5 g or more per 60 Kg of body weight of the human individual; and
(d) selecting a time and amount of isomaltulose ingestion reduce the increase in the human individual's blood glucose level in response to ingesting the isomaltulose compared to the increase in the human individual's blood glucose level absent the human individual ingesting the isomaltulose.

8. A method for reducing the blood glucose level increase in a human caused by consuming a carbohydrate, the method comprising the steps of:
(a) providing a reducer of blood glucose level increase, wherein the reducer comprises isomaltulose as an active ingredient;
(b) having a human individual ingest the reducer of blood glucose level increase;
(c) having the human individual consume 50 g to 150 g of the carbohydrate, wherein the reducer is ingested separately up to 30 minutes before consuming the carbohydrate, or simultaneously with consuming the carbohydrate, or separately after consuming the carbohydrate within a time range within which the isomaltulose and carbohydrate can be mixed in the stomach, and wherein the carbohydrate has an $\alpha$-1,6-glucosyl bond ratio of from 0% to less than 50% relative to the total bonds among constituent saccharides,
wherein the weight of the isomaltulose has a ratio of 10% or more relative to the total weight of the carbohydrate, and the isomaltulose is combined in the reducer so that the isomaltulose is ingested by the human individual in a dosed amount of 5 g or more per 60 Kg of body weight of the human individual; and
(d) selecting a time and amount of isomaltulose ingestion to reduce the increase in the human individual's blood glucose level in response to ingesting the isomaltulose compared to the increase in the human individual's blood glucose level absent the human individual ingesting the isomaltulose.

9. A method for reducing the blood glucose level increase in a human caused by consuming a food, the method comprising the steps of:
(a) providing a reducer of blood glucose level increase, wherein the reducer comprises isomaltulose as an active ingredient;
(b) having a human individual ingest the reducer of blood glucose level increase;
(c) having the human individual consume a food comprising a carbohydrate, wherein the reducer is ingested substantially with the food, and wherein the carbohydrate has an $\alpha$-1,6-glucosyl bond ratio of from 0% to less than 50% relative to the total bonds among constituent saccharides, and the isomaltulose is combined in the reducer so that the isomaltulose is ingested by the human individual in a dosed amount of 5 g or more per 60 Kg of body weight of the human individual, and
(d) selecting a time and amount of isomaltulose ingestion to reduce the increase in the human individual's blood glucose level in response to ingesting the isomaltulose compared to the increase in the human individual's blood glucose level absent the human individual ingesting the isomaltulose.

10. A method for reducing the blood glucose level increase in a human caused by consuming a carbohydrate, the method comprising the steps of:
(a) providing a reducer of blood glucose level increase, wherein the reducer comprises isomaltulose as an active ingredient;
(b) having a human individual ingest the reducer of blood glucose level increase;
(c) having the human individual consume the carbohydrate, wherein the reducer is ingested substantially with the carbohydrate, and wherein the carbohydrate has an $\alpha$-1,6-glucosyl bond ratio of from 0% to less than 50% relative to the total bonds among constituent saccharides, and the isomaltulose is corribined in the reducer so that the isomaltulose is in rested by the human individual in a dosed amount of 5 g or more per 60 Kg of body weight of the human individual; and
(d) selecting a time and amount of isomaltulose ingestion to reduce the increase in the human individual's blood glucose level in response to ingesting the reducer compared to the increase in the human individual's blood glucose level absent the human individual ingesting the reducer.

11. A method for reducing the blood glucose level increase in a human caused by consuming food, the method comprising the steps of:
(a) providing a reducer of blood glucose level increase, wherein the reducer comprises isomaltulose as an active ingredient;

(b) having a human individual ingest the reducer of blood glucose level increase;

(c) having the human individual consume a food comprising a carbohydrate, wherein the reducer is ingested substantially with consuming the food, and wherein the carbohydrate has an α-1,6-glucosyl bond ratio of from 0% to less than 50% relative to the total bonds among constituent saccharides, and wherein the food consumed includes 50 g to 150 g of the carbohydrate, wherein the weight of the isomaltulose has a ratio of 10% or more relative to the total weight of the carbohydrate, and the isomaltulose is corribined in the reducer so that the isomaitulose is ingested by the human individual in a dosed amount of 5 g or more per 60 Kg of body weight of the human individual; and (d) selecting a time and amount of isomaltulose ingestion to reducer the increase in the human individual's blood glucose level in response to ingesting the isomaltulose compared to the increase in the human individual's blood glucose level absent the human individual ingesting the isomaltulose.

12. A method for reducing the blood glucose level increase in a human caused by consuming a carbohydrate, the method comprising the steps of:

(a) providing a reducer of blood glucose level increase, wherein the reducer comprises isomaltulose as an active ingredient;

(b) having a human individual ingest the reducer of blood glucose level increase;

(c) having the human individual consume 50 g to 150 g of the carbohydrate, wherein the reducer is ingested substantially with the carbohydrate, and wherein the carbohydrate has an α-1,6-glucosyl bond ratio of from 0% to less than 50% relative to the total bonds among constituent saccharides, wherein the weight of the isomaltulose has a ratio of 10% or more relative to the total weight of the carbohydrate, and the isomaltulose is combined in the reducer so that the isomaltulose is ingested by the human individual in a dosed amount of 5 g or more per 60 Kg of body weight of the human individual; and (d) selecting a time and amount of isomaltulose ingestion to reduce the increase in the human individual's blood glucose level in response to ingesting the isomaltulose compared to the increase in the human individual's blood glucose level absent the human individual ingesting the isomaltulose.

13. A method for reducing the blood glucose level increase in a human caused by consuming food, the method comprising the steps of:

(a) providing a reducer of blood glucose level increase, wherein the reducer comprises isomaltulose as an active ingredient;

(b) having a human individual ingest the reducer of blood glucose level increase;

(c) having the human individual consume a food, comprising carbohydrate, wherein the carbohydrate includes at least one carbohydrate that lacks α-1,6-glucosyl bonds, wherein the carbohydrate includes a sufficient amount of the at least one carbohydrate that lacks α-1,6-glucosyl bonds to increase blood glucose level in the human after consumption of the food, and the isomaltulose is combined in the reducer so that the isomaltulose is ingested by the human individual in an amount of 5 g or more per 60 Kg of body weight of the human individual; and (d) selecting a time and amount of isomaltulose ingestion to reduce the increase in the human individual's blood glucose level in response to ingesting the isomaltulose compared to the increase in the human individual's blood glucose level absent the human individual ingesting the isomaltulose.

14. The method according to claim 13, wherein the carbohydrate includes glucose and sucrose.

15. The method according to claim 13, wherein the carbohydrate includes glucose.

16. The method according to claim 13, wherein the carbohydrate includes sucrose.

* * * * *